US006599910B1

(12) United States Patent
Adams et al.

(10) Patent No.: US 6,599,910 B1
(45) Date of Patent: Jul. 29, 2003

(54) SUBSTITUTED TRIAZOLE COMPOUNDS

(75) Inventors: Jerry L. Adams, Wayne, PA (US); Dennis Lee, Swathmore, PA (US)

(73) Assignee: SmithKline Beecham Corporation, Philadelphia, PA (US)

(*) Notice: Subject to any disclaimer, the term of this patent is extended or adjusted under 35 U.S.C. 154(b) by 0 days.

(21) Appl. No.: 09/762,809

(22) PCT Filed: Aug. 17, 1999

(86) PCT No.: PCT/US99/18640

§ 371 (c)(1),
(2), (4) Date: Jun. 11, 2001

(87) PCT Pub. No.: WO00/01563

PCT Pub. Date: Mar. 2, 2000

Related U.S. Application Data

(60) Provisional application No. 60/097,322, filed on Aug. 20, 1998, provisional application No. 60/097,302, filed on Aug. 20, 1998, and provisional application No. 60/097,300, filed on Aug. 20, 1998.

(51) Int. Cl.[7] ............... C07D 207/08; C07D 213/63; C07D 233/54; A61K 31/34; A61K 31/405
(52) U.S. Cl. ............... 514/275; 544/333; 544/284; 546/304; 546/272.4; 514/274; 514/340
(58) Field of Search ............... 546/272.4, 304; 514/340, 275, 274; 544/333, 284

(56) References Cited

FOREIGN PATENT DOCUMENTS

| | | |
|---|---|---|
| AU | 40230/85 | 3/1984 |
| DE | 0162217 | * 3/1985 |
| EP | 0 612 217 | 3/1985 |
| WO | WO 91/19497 | 12/1991 |
| WO | WO 92/10190 | 6/1992 |
| WO | WO 92/10498 | 6/1992 |
| WO | WO 93/14081 | 7/1993 |
| WO | WO 93/14082 | 7/1993 |
| WO | WO 95/03297 | 2/1995 |
| WO | WO 95/13067 | 5/1995 |
| WO | WO 95/02591 | 7/1995 |
| WO | WO 95/33461 | 12/1995 |
| WO | WO 96/21452 | 7/1996 |
| WO | WO 96/21654 | 7/1996 |
| WO | WO 96/40143 | 12/1996 |
| WO | WO 97/23479 | 7/1997 |
| WO | WO 97/25045 | 7/1997 |
| WO | WO 97/25046 | 7/1997 |
| WO | WO 97/25047 | 7/1997 |
| WO | WO 97/25048 | 7/1997 |
| WO | WO 97/32583 | 9/1997 |
| WO | WO 97/33883 | 9/1997 |
| WO | WO 97/35855 | 10/1997 |
| WO | WO 97/35856 | 10/1997 |
| WO | WO 98/06715 | 2/1998 |
| WO | WO 98/07425 | 2/1998 |
| WO | WO 98/16230 | 2/1998 |
| WO | WO 98/25619 | 6/1998 |
| WO | WO 98/28292 | 7/1998 |
| WO | WO 99/01131 | 1/1999 |
| WO | WO 99/01136 | 1/1999 |
| WO | WO 99/01452 | 1/1999 |
| WO | WO 99/17776 | 4/1999 |
| WO | WO 99/18942 | 4/1999 |
| WO | WO 99/32121 | 7/1999 |
| WO | WO 99/61437 | 12/1999 |
| WO | WO 99/61440 | 12/1999 |
| WO | WO 99/64400 | 12/1999 |
| WO | WO 00/01688 | 1/2000 |
| WO | WO 00/10563 | 3/2000 |
| WO | WO 00/19824 | 4/2000 |
| WO | WO 00/25791 | 5/2000 |

OTHER PUBLICATIONS

T.F. Gallagher et al., "Regulation of Stress–Induced Cytokine Production by Pyridinylimidazoles; Inhibition of CSBP Kinase", *Bioorganic & Medicinal Chemistry*, 1997, vol. 5, No. 1, pp. 49–64.

K.P. Wilson et al., "The structural basis for the specificity of pyridinyliumidazole inhibitors of p38 MAP kinase", *Chemistry & Biology*, 1997, vol. 4, No. 6, pp. 423–431.

J. C. Boehm et al., "1–Substitued 4–Aryl–5–pyridinylimidazoles: A new Class of Cytokine Suppressive Drugs with Low 5–Lipoxygnase and Cyclooxygenase Inhibitory Potency", *Journal of Medicinal Chemistry*, 1996, vol. 39, No. 20, pp. 3929–3937.

* cited by examiner

Primary Examiner—Bruck Kifle
Assistant Examiner—Hong Liu
(74) Attorney, Agent, or Firm—Dara L. Dinner; Stephen Venetianer; Charles M. Kinzig

(57) ABSTRACT

Novel substitued triazole compounds and compositions for use in therapy as CSBP/p38 kinase inhibitors.

26 Claims, 2 Drawing Sheets

SUBSTITUTED TRIAZOLE COMPOUNDS

This application claims benefit of U.S. Provision No. 60/097,322, filed Aug. 20, 1998, U.S. Provision No. 60/097,300, filed Aug. 20, 1998, U.S. Provision No. 60/097,302, filed Aug. 20, 1998.

FIELD OF THE INVENTION

This invention relates to a novel group of triazole compounds, processes for the preparation thereof, the use thereof in treating CSBP/p38 kinase mediated diseases and pharmaceutical compositions for use in such therapy.

BACKGROUND OF THE INVENTION

Intracellular signal transduction is the means by which cells respond to extracellular stimuli. Regardless of the nature of the cell surface receptor (e.g. protein tyrosine kinase or seven-transmembrane G-protein coupled), protein kinases and phosphatases along with phopholipases are the essential machinery by which the signal is further transmitted within the cell [Marshall, J. C. Cell, 80, 179–278 (1995)]. Protein kinases can be categorized into five classes with the two major classes being, tyrosine kinases and serine/threonine kinases depending upon whether the enzyme phosphorylates its substrate(s) on specific tyrosine (s) or serine/threonine(s) residues [Hunter, T., Methods in Enzymology (Protein Kinase Classification) p. 3, Hunter, T.; Sefton, B. M.; eds. vol. 200, Academic Press; San Diego, 1991].

For most biological responses, multiple intracellular kinases are involved and an individual kinase can be involved in more than one signaling event. These kinases are often cytosolic and can translocate to the nucleus or the ribosomes where they can affect transcriptional and translational events, respectively. The involvement of kinases in transcriptional control is presently much better understood than their effect on translation as illustrated by the studies on growth factor induced signal transduction involving MAP/ERK kinase [Marshall, C. J. Cell, 80, 179 (1995); Herskowitz, I. Cell, 80, 187 (1995); Hunter, T. Cell, 80, 225 (1995); Seger, R., and Krebs, E. G. FASEB J., 726–735 (1995)].

While many signaling pathways are part of cell homeostasis, numerous cytokines (e.g., IL-1 and TNF) and certain other mediators of inflammation (e.g., COX-2, and iNOS) are produced only as a response to stress signals such as bacterial lipopolysaccharide (LPS). The first indications suggesting that the signal transduction pathway leading to LPS-induced cytokine biosynthesis involved protein kinases came from studies of Weinstein [Weinstein, et al., J. Immunol. 151, 3829(1993)] but the specific protein kinases involved were not identified. Working from a similar perspective, Han [Han, et al., Science 265, 808(1994)] identified murine p38 as a kinase which is tyrosine phosphorylated in response to LPS. Definitive proof of the involvement of the p38 kinase in LPS-stimulated signal transduction pathway leading to the initiation of proinflammatory cytokine biosynthesis was provided by the independent discovery of p38 kinase by Lee [Lee; et al., Nature, 372, 739(1994)] as the molecular target for a novel class of anti-inflammatory agents. The discovery of p38 (termed by Lee as CSBP 1 and 2) provided a mechanism of action of a class of anti-inflammatory compounds for which SK&F 86002 was the prototypic example. These compounds inhibited IL-1 and TNF synthesis in human monocytes at concentrations in the low uM range [Lee, et al., Int. J. Immunopharmac. 10(7), 835(1988)] and exhibited activity in animal models which are refractory to cyclooxygenase inhibitors [Lee; et al., Annals N.Y. Acad. Sci., 696, 149 (1993)].

It is now firmly established that CSBP/p38 is a one of several kinases involved in a stress-response signal transduction pathway which is parallel to and largely independent of the analogous mitogen-activated protein kinase (MAP) kinase cascade (FIG. 1). Stress signals, including LPS, pro-inflammatory cytokines, oxidants, UV light and osmotic stress, activate kinases upstream from CSBP/p38 which in turn phosphorylate CSBP/p38 at threonine 180 and tyrosine 182 resulting in CSBP/p38 activation. MAPKAP kinase-2 and MAPKAP kinase-3 have been identified as downstream substrates of CSBP/p38 which in turn phosphorylate heat shock protein Hsp 27 (FIG. 2). It is not yet known whether MAPKAP-2, MAPKAP-3, Mnk1 or Mnk2 are involved in cytokine biosynthesis or alternatively that inhibitors of CSBP/p38 kinase might regulate cytokine biosynthesis by blocking a yet unidentified substrate downstream from CSBP/p38 [Cohen, P. Trends Cell Biol., 353–361(1997)].

What is known, however, is that in addition to inhibiting IL-1 and TNF CSBP/p38 kinase inhibitors (SK&F 86002 and SB 203580) also decrease the synthesis of a wide variety of pro-inflammatory proteins including, IL-6, IL-8, GM-CSF and COX-2. Inhibitors of CSBP/p38 kinase have also been shown to suppress the TNF-induced expression of VCAM-1 on endothelial cells, the TNF-induced phosphorylation and activation of cytosolic PLA2 and the IL-1-stimulated synthesis of collagenase and stromelysin. These and additional data demonstrate that CSBP/p38 is involved not only cytokine synthesis, but also in cytokine signaling [CSBP/P38 kinase reviewed in Cohen, P. Trends Cell Biol., 353–361(1997)].

Interleukin-1 (IL-1) and Tumor Necrosis Factor (TNF) are biological substances produced by a variety of cells, such as monocytes or macrophages. IL-1 has been demonstrated to mediate a variety of biological activities thought to be important in immunoregulation and other physiological conditions such as inflammation [See, e.g., Dinarello et al., Rev. Infect. Disease, 6, 51 (1984)]. The myriad of known biological activities of IL-1 include the activation of T helper cells, induction of fever, stimulation of prostaglandin or collagenase production, neutrophil chemotaxis, induction of acute phase proteins and the suppression of plasma iron levels.

There are many disease states in which excessive or unregulated IL-1 production is implicated in exacerbating and/or causing the disease. These include rheumatoid arthritis, osteoarthritis, endotoxemia and/or toxic shock syndrome, other acute or chronic inflammatory disease states such as the inflammatory reaction induced by endotoxin or inflammatory bowel disease; tuberculosis, atherosclerosis, muscle degeneration, cachexia, psoriatic arthritis, Reiter's syndrome, rheumatoid arthritis, gout, traumatic arthritis, rubella arthritis, and acute synovitis. Recent evidence also links IL-1 activity to diabetes and pancreatic β cells [review of the biological activities which have been attributed to IL-1 Dinarello, J. Clinical Immunology, 5 (5), 287–297 (1985)].

Excessive or unregulated TNF production has been implicated in mediating or exacerbating a number of diseases including rheumatoid arthritis, rheumatoid spondylitis, osteoarthritis, gouty arthritis and other arthritic conditions; sepsis, septic shock, endotoxic shock, gram negative sepsis, toxic shock syndrome, adult respiratory distress syndrome, cerebral malaria, chronic pulmonary inflammatory disease, silicosis, pulmonary sarcoisosis, bone resorption diseases, reperfusion injury, graft vs. host reaction, allograft rejections, fever and myalgias due to infection, such as influenza, cachexia secondary to infection or malignancy, cachexia, secondary to acquired immune deficiency syndrome (AIDS), AIDS, ARC (AIDS related complex), keloid formation, scar tissue formation, Crohn's disease, ulcerative colitis, or pyresis.

Interleukin-8 (IL-8) is a chemotactic factor produced by several cell types including mononuclear cells, fibroblasts, endothelial cells, and keratinocytes. Its production from endothelial cells is induced by IL-1, TNF, or lipopolysaccharide (LPS). IL-8 stimulates a number of functions in vitro. It has been shown to have chemoattractant properties for neutrophils, T-lymphocytes, and basophils. In addition it induces histamine release from basophils from both normal and atopic individuals as well as lysozomal enzyme release and respiratory burst from neutrophils. IL-8 has also been shown to increase the surface expression of Mac-1 (CD11b/CD18) on neutrophils without de novo protein synthesis, this may contribute to increased adhesion of the neutrophils to vascular endothelial cells. Many diseases are characterized by massive neutrophil infiltration. Conditions associated with an increased in IL-8 production (which is responsible for chemotaxis of neutrophil into the inflammatory site) would benefit by compounds which are suppressive of IL-8 production.

IL-1 and TNF affect a wide variety of cells and tissues and these cytokines as well as other leukocyte derived cytokines are important and critical inflammatory mediators of a wide variety of disease states and conditions. The inhibition of these cytokines is of benefit in controlling, reducing and alleviating many of these disease states.

Inhibition of signal transduction via CSBP/p38, which in addition to IL-1, TNF and IL-8 described above is also required for the synthesis and/or action of several additional pro-inflammatory proteins (i.e., IL-6, GM-CSF, COX-2, collagenase and stromelysin), is expected to be a highly effective mechanism for regulating the excessive and destructive activation of the immune system. This expectation is supported by the potent and diverse anti-inflammatory activities described for CSBP/p38 kinase inhibitors [Badger, et al., *J. Pharm. Exp. Thera.* 279 (3): 1453–1461.(1996); Griswold, et al, *Pharmacol. Comm.* 7, 323–229 (1996)].

There remains a need for treatment, in this field, for compounds which are cytokine suppressive anti-inflammatory drugs, i.e. compounds which are capable of inhibiting the CSBP/p38/RK kinase.

SUMMARY OF THE INVENTION

Figure 1:
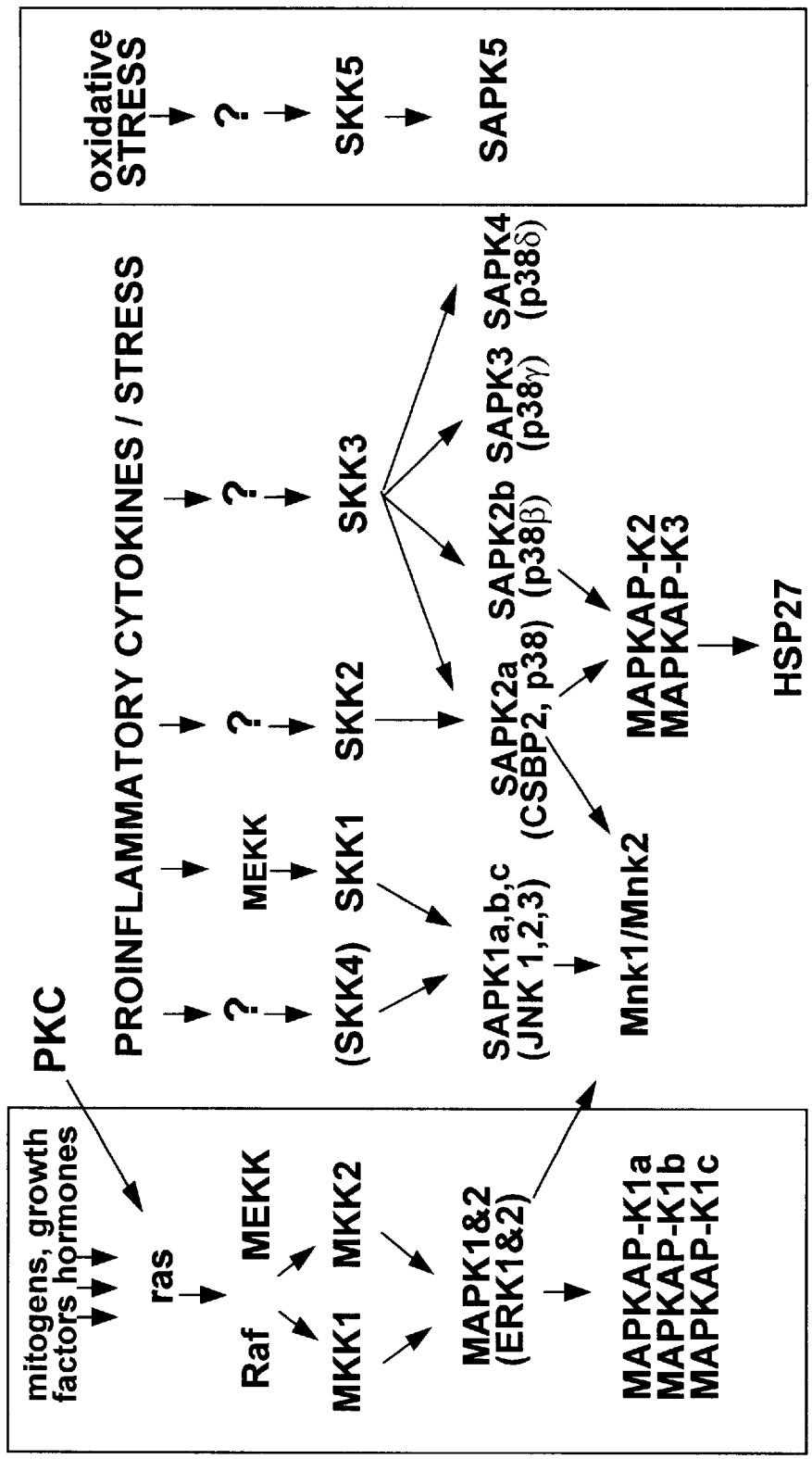
FIG. 1 demonstrates the mitogen-activated protein kinase (MAP) kinase cascade.
Figure 2:
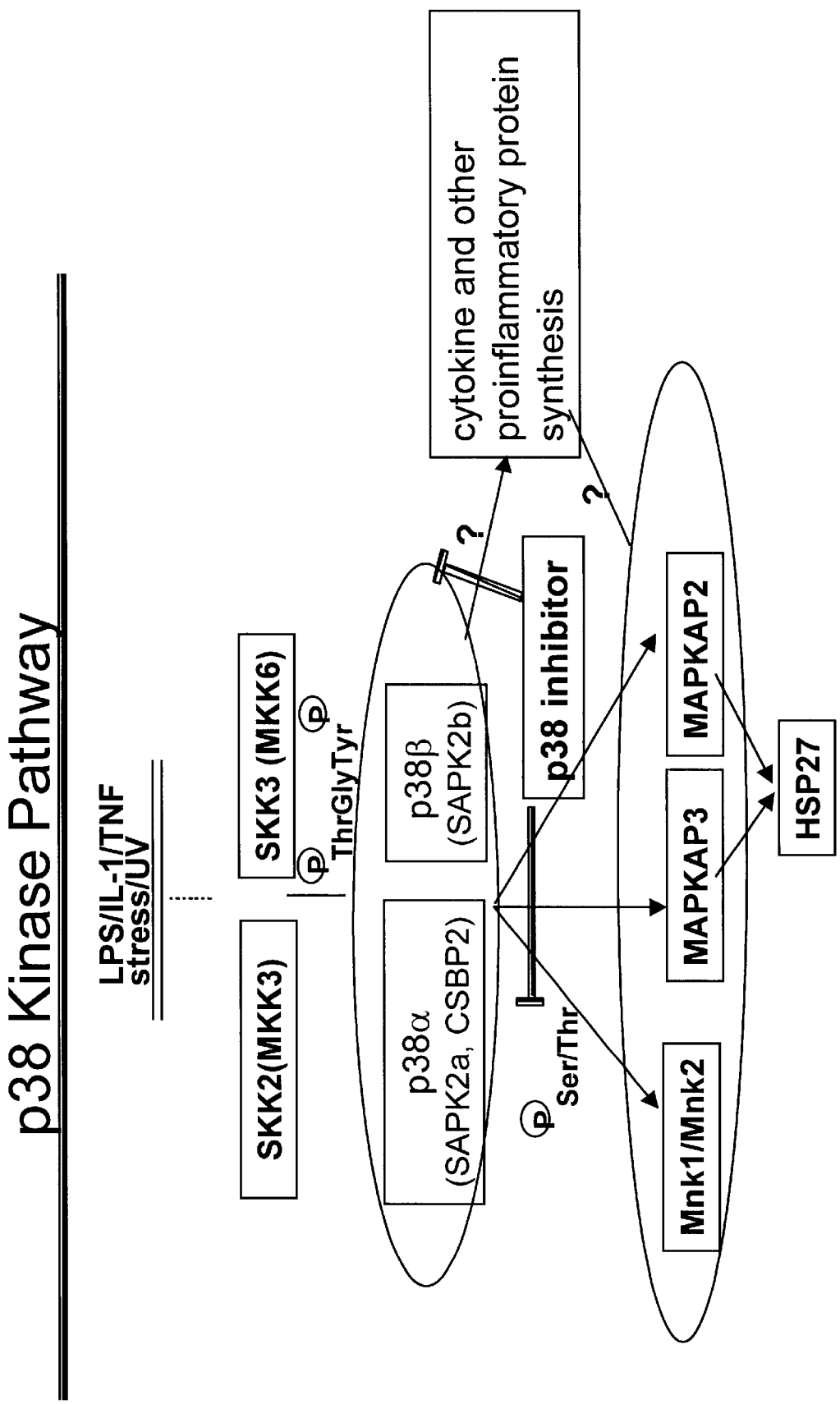
FIG. 2 demonstrates the p38 kinase pathway.

This invention relates to the novel compounds of Formula (I), (II) and (III) and pharmaceutical compositions comprising a compound of Formula (I), (II) or (III) and a pharmaceutically acceptable diluent or carrier.

This invention relates to a method of treating a CSBP/RK/p38 kinase mediated disease in a mammal in need thereof, which comprises administering to said mammal an effective amount of a compound of Formula (I), (II) or (III).

This invention also relates to a method of inhibiting cytokines and the treatment of a cytokine mediated disease, in a mammal in need thereof, which comprises administering to said mammal an effective amount of a compound of Formula (I), (II) or (III).

This invention more specifically relates to a method of inhibiting the production of IL-1 in a mammal in need thereof which comprises administering to said mammal an effective amount of a compound of Formula (I), (II) or (III).

This invention more specifically relates to a method of inhibiting the production of IL-6 in a mammal in need thereof which comprises administering to said mammal an effective amount of a compound of Formula (I), (II) or (III).

This invention more specifically relates to a method of inhibiting the production of IL-8 in a mammal in need thereof which comprises administering to said mammal an effective amount of a compound of Formula (I), (II) or (III).

This invention more specifically relates to a method of inhibiting the production of TNF in a mammal in need thereof which comprises administering to said mammal an effective amount of a compound of Formula (I), (II), or (III).

Accordingly, the present invention provides a compound of Formula (I):

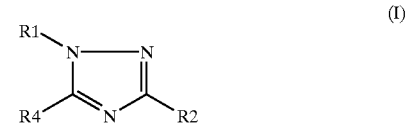

(I)

wherein
$R_1$ is pyrid-4-yl, or pyrimidin-4-yl ring, which ring is optionally substituted one or more times with Y, $C_{1-4}$ alkyl, halogen, hydroxyl, $C_{1-4}$ alkoxy, $C_{1-4}$ alkylthio, $C_{1-4}$ alkylsulfinyl, $CH_2OR_{12}$, amino, mono and di-$C_{1-6}$ alkyl substituted amino, or a N-heterocyclyl ring which ring has from 5 to 7 members and optionally contains an additional heteroatom selected from oxygen, sulfur or $NR_{15}$, or $N(R_{10})C(O)R_b$;

Y is $X_1$-$R_a$;

$X_1$ is sulfur, oxygen, or NH;

$R_a$ is $C_{1-6}$alkyl, aryl, aryl$C_{1-6}$alkyl, heterocyclic, heterocyclyl$C_{1-6}$ alkyl, heteroaryl, or heteroaryl$C_{1-6}$alkyl; and wherein each of these moieties may be optionally substituted;

$R_4$ is phenyl, naphth-1-yl or naphth-2-yl, or a heteroaryl, which is optionally substituted by one or two substituents, each of which is independently selected, and which, for a 4-phenyl, 4-naphth-1-yl, 5-naphth-2-yl or 6-naphth-2-yl substituent, is halogen, cyano, nitro, $C(Z)NR_7R_{17}$, $C(Z)OR_{16}$, $(CR_{10}R_{20})_vCOR_{12}$, $SR_5$, $SOR_5$, $OR_{12}$, halo-substituted-$C_{1-4}$ alkyl, $C_{1-4}$ alkyl, $ZC(Z)R_{12}$, $NR_{10}C(Z)R_{16}$, or $(CR_{10}R_{20})_vNR_{10}R_{20}$ and which, for other positions of substitution, is halogen, cyano, $C(Z)NR_{13}R_{14}$, $C(Z)OR_3$, $(CR_{10}R_{20})_{m''}COR_3$, $S(O)_mR_3$, $OR_3$, halo-substituted-$C_{1-4}$ alkyl, $C_{1-4}$ alkyl, $(CR_{10}R_{20})_{m''}NR_{10}C(Z)R_3$, $NR_{10}S(O)_{m'}R_8$, $NR_{10}S(O)_{m'}NR_7R_{17}$, $ZC(Z)R_3$ or $(CR_{10}R_{20})_{m''}NR_{13}R_{14}$;

Z is oxygen or sulfur;

n is 0, or an integer having a value of 1 to 10;

m is 0, or the integer 1 or 2;

m' is an integer having a value of 1 or 2, m" is 0, or an integer having a value of 1 to 5;

v is 0, or an integer having a value of 1 or 2;

R$_2$ is hydrogen, C(H)(A)(R$_{22}$), (CR$_{10}$R$_{23}$)$_n$OR$_9$, (CR$_{10}$R$_{23}$)$_n$OR$_{11}$, C$_{1-10}$alkyl, halo-substituted C$_{1-10}$ alkyl, C$_{2-10}$ alkenyl, C$_{2-10}$ alkynyl, C$_{3-7}$ cycloalkyl, C$_{3-7}$cycloalkylC$_{1-10}$ alkyl, C$_{5-7}$ cycloalkenyl, C$_{5-7}$ cycloalkenyl C$_{1-10}$alkyl, aryl, arylC$_{1-10}$ alkyl, heteroaryl, heteroarylC$_{1-10}$alkyl, heterocyclyl, heterocyclylC$_{1-10}$ alkyl, (CR$_{10}$R$_{23}$)$_n$S(O)$_m$R$_{18}$, (CR$_{10}$R$_{23}$)$_n$NHS(O)$_2$R$_{18}$, (CR$_{10}$R$_{23}$)$_n$NR$_{13}$R$_{14}$, (CR$_{10}$R$_{23}$)$_n$NO$_2$, (CR$_{10}$R$_{23}$)$_n$CN, (CR$_{10}$R$_{23}$)$_n$S(O)$_{m'}$NR$_{13}$R$_{14}$, (CR$_{10}$R$_{230}$)$_n$C(Z)R$_{11}$, (CR$_{10}$R$_{23}$)$_n$OC(Z)R$_{11}$, (CR$_{10}$R$_{23}$)$_n$C(Z)OR$_{11}$, (CR$_{10}$R$_{23}$)$_n$C(Z)NR$_{13}$R$_{14}$, (CR$_{10}$R$_{23}$)$_n$C(Z)NR$_{11}$OR$_9$, (CR$_{10}$R$_{23}$)$_n$NR$_{10}$C(Z)R$_{11}$, (CR$_{10}$R$_{23}$)$_n$NR$_{10}$C(Z)NR$_{13}$R$_{14}$, (CR$_{10}$R$_{23}$)$_n$N(OR$_6$)C(Z)NR$_{13}$R$_{14}$, (CR$_{10}$R$_{23}$)$_n$N(OR$_6$)C(Z)R$_{11}$, (CR$_{10}$R$_{23}$)$_n$C(=NOR$_6$)R$_{11}$, (CR$_{10}$R$_{23}$)$_n$NR$_{10}$C(=NR$_{19}$)NR$_{13}$R$_{14}$, (CR$_{10}$R$_{23}$)$_n$OC(Z)NR$_{13}$R$_{14}$, (CR$_{10}$R$_{23}$)$_n$NR$_{10}$C(Z)NR$_{13}$R$_{14}$, (CR$_{10}$R$_{23}$)$_n$NR$_{10}$C(Z)OR$_{10}$, 5-(R$_{18}$)-1,2,4-oxadizaol-3-yl or 4-(R$_{12}$)-5-(R$_{18}$R$_{19}$)-4,5-dihydro-1,2,4-oxadiazol-3-yl; and wherein the cycloalkyl, cycloalkyl alkyl, aryl, arylalkyl, heteroaryl, heteroaryl alkyl, heterocyclic and heterocyclic alkyl groups may be optionally substituted;

A is an optionally substituted aryl, heterocyclyl, or heteroaryl ring, or A is a substituted C$_{1-10}$ alkyl;

R$_{22}$ is an optionally substituted C$_{1-10}$ alkyl;

R$_b$ is hydrogen, C$_{1-6}$ alkyl, C$_{3-7}$ cycloalkyl, aryl, arylC$_{1-4}$ alkyl, heteroaryl, heteroarylC$_{1-4}$alkyl, heterocyclyl, or heterocyclylC$_{1-4}$ alkyl; and wherein each of these moieties may be optionally substituted;

R$_3$ is heterocyclyl, heterocyclylC$_{1-10}$ alkyl or R$_8$;

R$_5$ is hydrogen, C$_{1-4}$ alkyl, C$_{2-4}$ alkenyl, C$_{2-4}$ alkynyl or NR$_7$R$_{17}$, excluding the moieties SR$_5$ being SNR$_7$R$_{17}$ and SOR$_5$ being SOH;

R$_6$ is hydrogen, a pharmaceutically acceptable cation, C$_{1-10}$ alkyl, C$_{3-7}$ cycloalkyl, aryl, arylC$_{1-4}$ alkyl, heteroaryl, heteroarylC$_{1-4}$ alkyl, heterocyclic, aroyl, or C$_{1-10}$ alkanoyl;

R$_7$ and R$_{17}$ is each independently selected from hydrogen or C$_{1-4}$ alkyl or R$_7$ and R$_{17}$ together with the nitrogen to which they are attached form a heterocyclic ring of 5 to 7 members which ring optionally contains an additional heteroatom selected from oxygen, sulfur or NR$_{15}$;

R$_8$ is C$_{1-10}$ alkyl, halo-substituted C$_{1-10}$ alkyl, C$_{2-10}$ alkenyl, C$_{2-10}$ alkynyl, C$_{3-7}$ cycloalkyl, C$_{5-7}$ cycloalkenyl, aryl, arylC$_{1-10}$ alkyl, heteroaryl, heteroarylC$_{1-10}$ alkyl, (CR$_{10}$R$_{20}$)$_n$OR$_{11}$, (CR$_{10}$R$_{20}$)$_n$S(O)$_m$R$_{18}$, (CR$_{10}$R$_{20}$)$_n$NHS(O)$_2$R$_{18}$, or (CR$_{10}$R$_{20}$)$_n$NR$_{13}$R$_{14}$; and wherein the aryl, arylalkyl, heteroaryl, heteroaryl alkyl may be optionally substituted;

R$_9$ is hydrogen, C(Z)R$_{11}$ or optionally substituted C$_{1-10}$ alkyl, S(O)$_2$R$_{18}$, optionally substituted aryl or optionally substituted aryl-C$_{1-4}$ alkyl;

R$_{10}$ and R$_{20}$ are each independently selected from hydrogen or C$_{1-4}$ alkyl;

R$_{11}$ is hydrogen, C$_{1-10}$ alkyl, C$_{3-7}$ cycloalkyl, heterocyclyl, heterocyclyl C$_{1-10}$alkyl, aryl, arylC$_{1-10}$ alkyl, heteroaryl or heteroarylC$_{1-10}$ alkyl, wherein these moieties may be optionally substituted;

R$_{12}$ is hydrogen or R$_{16}$;

R$_{13}$ and R$_{14}$ is each independently selected from hydrogen or optionally substituted C$_{1-4}$ alkyl, optionally substituted aryl or optionally substituted aryl-C$_{1-4}$ alkyl, or together with the nitrogen which they are attached form a heterocyclic ring of 5 to 7 members which ring optionally contains an additional heteroatom selected from oxygen, sulfur or NR$_9$;

R$_{15}$ is R$_{10}$ or C(Z)-C$_{1-4}$ alkyl;

R$_{16}$ is C$_{1-4}$ alkyl, halo-substituted-C$_{1-4}$ alkyl, or C$_{3-7}$ cycloalkyl;

R$_{18}$ is C$_{1-10}$ alkyl, C$_{3-7}$ cycloalkyl, heterocyclyl, aryl, aryl$_{1-10}$alkyl, heterocyclyl, heterocyclyl-C$_{1-10}$alkyl, heteroaryl or heteroaryl$_{1-10}$alkyl;

R$_{19}$ is hydrogen, cyano, C$_{1-4}$ alkyl, C$_{3-7}$ cycloalkyl or aryl;

R$_{23}$ is hydrogen, C$_{1-6}$ alkyl, C$_{3-7}$ cycloalkyl, aryl, arylC$_{1-4}$ alkyl, heteroaryl, heteroarylC$_{1-4}$alkyl, heterocyclyl, or heterocyclylC$_{1-4}$ alkyl moiety, all of which may be optionally substituted;

or a pharmaceutically acceptable salt thereof.

DETAILED DESCRIPTION OF THE INVENTION

Another aspect of the present invention are the novel compounds of Formula (II) represented by the structure:

Accordingly, the present invention provides for a compound of Formula (II):

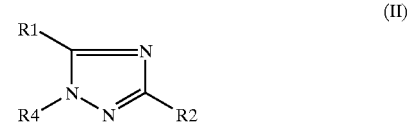

(II)

wherein

R$_1$ is a pyrid-4-yl, or pyrimidin-4-yl ring, which ring is optionally substituted one or more times with Y, C$_{1-4}$ alkyl, halogen, hydroxyl, C$_{1-4}$ alkoxy, C$_{1-4}$alkylthio, C$_{1-4}$ alkylsulfinyl, CH$_2$OR$_{12}$, amino, mono and di-C$_{1-6}$ alkyl substituted amino, or a N-heterocyclyl ring which ring has from 5 to 7 members and optionally contains an additional heteroatom selected from oxygen, sulfur or NR$_{15}$, or N(R$_{10}$)C(O)R$_b$;

Y is X$_1$-R$_a$;

X$_1$ is sulfur, oxygen, or NH;

R$_a$ is C$_{1-6}$alkyl, aryl, arylC$_{1-6}$alkyl, heterocyclic, heterocyclylC$_{1-6}$ alkyl, heteroaryl, or heteroarylC$_{1-6}$alkyl, wherein each of these moieties may be optionally substituted;

R$_4$ is phenyl, naphth-1-yl or naphth-2-yl, or a heteroaryl, which is optionally substituted by one or two substituents, each of which is independently selected, and which, for a 4-phenyl, 4-naphth-1-yl, 5-naphth-2-yl or 6-naphth-2-yl substituent, is halogen, cyano, nitro, C(Z)NR$_7$R$_{17}$, C(Z)OR$_{16}$, (CR$_{10}$R$_{20}$)$_v$COR$_{12}$, SR$_5$, SOR$_5$, OR$_{12}$, halo-substituted-C$_{1-4}$ alkyl, C$_{1-4}$ alkyl, ZC(Z)R$_{12}$, NR$_{10}$C(Z)R$_{16}$, or (CR$_{10}$R$_{20}$)$_v$NR$_{10}$R$_{20}$ and which, for other positions of substitution, is halogen, cyano, C(Z)NR$_{13}$R$_{14}$, C(Z)OR$_3$, (CR$_{10}$R$_{20}$)$_{m''}$COR$_3$, S(O)$_m$R$_3$, OR$_3$, halo-substituted-C$_{1-4}$ alkyl, C$_{1-4}$ alkyl, (CR$_{10}$R$_{20}$)$_{m''}$NR$_{10}$C(Z)R$_3$, NR$_{10}$S(O)$_{m'}$R$_8$, NR$_{10}$S(O)$_{m'}$NR$_7$R$_{17}$, ZC(Z)R$_3$ or (CR$_{10}$R$_{20}$)$_{m''}$NR$_{13}$R$_{14}$;

Z is oxygen or sulfur;

n is 0, or an integer having a value of 1 to 10;

m is 0, or the integer 1 or 2;

m' is an integer having a value of 1 or 2, m" is 0, or an integer having a value of 1 to 5;

v is 0, or an integer having a value of 1 or 2;

R$_2$ is hydrogen, C(H)(A)(R$_{22}$), (CR$_{10}$R$_{23}$)$_n$OR$_9$, (CR$_{10}$R$_{23}$)$_n$OR$_{11}$, C$_{1-10}$alkyl, halo-substituted C$_{1-10}$ alkyl, $C_{2-10}$ alkenyl, $C_{2-10}$ alkynyl, $C_{3-7}$ cycloalkyl, $C_{3-7}$cycloalkyl$C_{1-10}$ alkyl, $C_{5-7}$ cycloalkenyl, $C_{5-7}$ cycloalkenyl $C_{1-10}$alkyl, aryl, aryl$C_{1-10}$ alkyl, heteroaryl, heteroaryl$C_{1-10}$alkyl, heterocyclyl, heterocyclyl$C_{1-10}$ alkyl, $(CR_{10}R_{23})_nS(O)_mR_{18}$, $(CR_{10}R_{23})_nNHS(O)_2R_{18}$, $(CR_{10}R_{23})_nNR_{13}R_{14}$, $(CR_{10}R_{23})_nNO_2$, $(CR_{10}R_{23})_nCN$, $(CR_{10}R_{23})_nS(O)_mNR_{13}R_{14}$, $(CR_{10}R_{230})_nC(Z)R_{11}$, $(CR_{10}R_{23})_nOC(Z)R_{11}$, $(CR_{10}R_{23})_nC(Z)OR_{11}$, $(CR_{10}R_{23})_nC(Z)NR_{13}R_{14}$, $(CR_{10}R_{23})_nC(Z)NR_{11}OR_9$, $(CR_{10}R_{23})_nNR_{10}C(Z)R_{11}$, $(CR_{10}R_{23})_nNR_{10}C(Z)NR_{13}R_{14}$, $(CR_{10}R_{23})_nN(OR_6)C(Z)NR_{13}R_{14}$, $(CR_{10}R_{23})_nN(OR_6)C(Z)R_{11}$, $(CR_{10}R_{23})_nC(=NOR_6)R_{11}$, $(CR_{10}R_{23})_nNR_{10}C(=NR_{19})NR_{13}R_{14}$, $(CR_{10}R_{23})_nOC(Z)NR_{13}R_{14}$, $(CR_{10}R_{23})_nNR_{10}C(Z)NR_{13}R_{14}$, $(CR_{10}R_{23})_nNR_{10}C(Z)OR_{10}$, 5-($R_{18}$)-1,2,4-oxadiazol-3-yl or 4-($R_{12}$)-5-($R_{18}R_{19}$)-4,5-dihydro-1,2,4-oxadiazol-3-yl; wherein the cycloalkyl, cycloalkyl alkyl, aryl, arylalkyl, heteroaryl, heteroaryl alkyl, heterocyclic and heterocyclic alkyl groups may be optionally substituted;

A is an optionally substituted aryl, heterocyclyl, or heteroaryl ring, or A is a substituted $C_{1-10}$ alkyl;

$R_{22}$ is an optionally substituted $C_{1-10}$ alkyl;

$R_b$ is hydrogen, $C_{1-6}$ alkyl, $C_{3-7}$ cycloalkyl, aryl, aryl$C_{1-4}$ alkyl, heteroaryl, heteroaryl$C_{1-4}$alkyl, heterocyclyl, or heterocyclyl$C_{1-4}$ alkyl; and wherein each of these moieties may be optionally substituted;

$R_3$ is heterocyclyl, heterocyclyl$C_{1-10}$ alkyl or $R_8$;

$R_5$ is hydrogen, $C_{1-4}$ alkyl, $C_{2-4}$ alkenyl, $C_{2-4}$ alkynyl or $NR_7R_{17}$, excluding the moieties $SR_5$ being $SNR_7R_{17}$ and $SOR_5$ being SOH;

$R_6$ is hydrogen, a pharmaceutically acceptable cation, $C_{1-10}$ alkyl, $C_{3-7}$ cycloalkyl, aryl, aryl$C_{1-4}$ alkyl, heteroaryl, heteroaryl$C_{1-4}$ alkyl, heterocyclic, aroyl, or $C_{1-10}$ alkanoyl;

$R_7$ and $R_{17}$ is each independently selected from hydrogen or $C_{1-4}$ alkyl or $R_7$ and $R_{17}$ together with the nitrogen to which they are attached form a heterocyclic ring of 5 to 7 members which optionally contains an additional heteroatom selected from oxygen, sulfur or $NR_{15}$;

$R_8$ is $C_{1-10}$ alkyl, halo-substituted $C_{1-10}$ alkyl, $C_{2-10}$ alkenyl, $C_{2-10}$ alkynyl, $C_{3-7}$ cycloalkyl, $C_{5-7}$ cycloalkenyl, aryl, aryl$C_{1-10}$ alkyl, heteroaryl, heteroaryl$C_{1-10}$ alkyl, $(CR_{10}R_{20})_nOR_{11}$, $(CR_{10}R_{20})_nS(O)_mR_{18}$, $(CR_{10}R_{20})_nNHS(O)_2R_{18}$, $(CR_{10}R_{20})_nNR_{13}R_{14}$; and wherein the aryl, arylalkyl, heteroaryl, and heteroarylalkyl moieties may be optionally substituted;

$R_9$ is hydrogen, $C(Z)R_{11}$ or optionally substituted $C_{1-10}$ alkyl, $S(O)_2R_{18}$, optionally substituted aryl or optionally substituted aryl-$C_{1-4}$ alkyl;

$R_{10}$ and $R_{20}$ are each independently selected from hydrogen or $C_{1-4}$ alkyl;

$R_{11}$ is hydrogen, $C_{1-10}$ alkyl, $C_{3-7}$ cycloalkyl, heterocyclyl, heterocyclyl $C_{1-10}$alkyl, aryl, aryl$C_{1-10}$ alkyl, heteroaryl or heteroaryl$C_{1-10}$ alkyl, wherein all of these moieties may be optionally substituted;

$R_{12}$ is hydrogen or $R_{16}$;

$R_{13}$ and $R_{14}$ is each independently selected from hydrogen or optionally substituted $C_{1-4}$ alkyl, optionally substituted aryl or optionally substituted aryl-$C_{1-4}$ alkyl, or together with the nitrogen which they are attached form a heterocyclic ring of 5 to 7 members which ring optionally contains an additional heteroatom selected from oxygen, sulfur or $NR_9$;

$R_{15}$ is $R_{10}$ or $C(Z)$-$C_{1-4}$ alkyl;

$R_{16}$ is $C_{1-4}$ alkyl, halo-substituted-$C_{1-4}$ alkyl, or $C_{3-7}$ cycloalkyl;

$R_{18}$ is $C_{1-10}$ alkyl, $C_{3-7}$ cycloalkyl, heterocyclyl, aryl, aryl$_{1-10}$alkyl, heterocyclyl, heterocyclyl-$C_{1-10}$alkyl, heteroaryl or heteroaryl$_{1-10}$alkyl;

$R_{19}$ is hydrogen, cyano, $C_{1-4}$ alkyl, $C_{3-7}$ cycloalkyl or aryl;

$R_{23}$ is hydrogen, $C_{1-6}$ alkyl, $C_{3-7}$ cycloalkyl, aryl, aryl$C_{1-4}$ alkyl, heteroaryl, heteroaryl$C_{1-4}$alkyl, heterocyclyl, or heterocyclyl$C_{1-4}$ alkyl moiety, all of which may be optionally substituted;

or a pharmaceutically acceptable salt thereof.

Another aspect of the present invention are the novel compounds of Formula (III) represented by the structure:

Accordingly, the present invention provides for a compound of Formula (III):

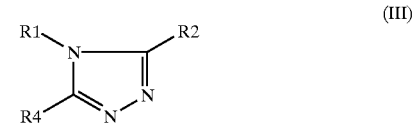

(III)

wherein $R_1$ is a pyrid-4-yl, or a pyrimidin-4-yl ring, which ring is optionally substituted one or more times with Y, $C_{1-4}$ alkyl, halogen, hydroxyl, $C_{1-4}$ alkoxy, $C_{1-4}$ alkylthio, $C_{1-4}$ alkylsulfinyl, $CH_2OR_{12}$, amino, mono and di-$C_{1-6}$ alkyl substituted amino, a N-heterocyclyl ring which ring has from 5 to 7 members and optionally contains an additional heteroatom selected from oxygen, sulfur or $NR_{15}$, or $N(R_{10})C(O)R_b$;

Y is $X_1$-$R_a$;

$X_1$ is sulfur, oxygen or NH;

$R_a$ is $C_{1-6}$alkyl, aryl, aryl$C_{1-6}$alkyl, heterocyclic, heterocyclyl$C_{1-6}$ alkyl, heteroaryl, or heteroaryl$C_{1-6}$alkyl, wherein each of these moieties may be optionally substituted;

$R_4$ is a phenyl, naphth-1-yl, naphth-2-yl, or a heteroaryl ring, which rings are optionally substituted by one or two substituents, each of which is independently selected, and which, for a 4-phenyl, 4-naphth-1-yl, 5-naphth-2-yl or 6-naphth-2-yl substituent, is halogen, cyano, nitro, $C(Z)NR_7R_{17}$, $C(Z)OR_{16}$, $(CR_{10}R_{20})_vCOR_{12}$, $SR_5$, $SOR_5$, $OR_{12}$, halo-substituted-$C_{1-4}$ alkyl, $C_{1-4}$alkyl, $ZC(Z)R_{12}$, $NR_{10}C(Z)R_{16}$, or $(CR_{10}R_{20})_vNR_{10}R_{20}$ and which, for other positions of substitution, is halogen, cyano, $C(Z)NR_{13}R_{14}$, $C(Z)OR_3$, $(CR_{10}R_{20})_{m"}COR_3$, $S(O)_mR_3$, $OR_3$, halo-substituted-$C_{1-4}$ alkyl, $C_{1-4}$ alkyl, $(CR_{10}R_{20})_{m"}NR_{10}C(Z)R_3$, $NR_{10}S(O)_{m'}R_8$, $NR_{10}S(O)_{m'}NR_7R_{17}$, $ZC(Z)R_3$ or $(CR_{10}R_{20})_{m"}NR13R_{14}$;

Z is oxygen or sulfur;

n is 0, or an integer having a value of 1 to 10;

m is 0, or the integer 1 or 2;

m' is an integer having a value of 1 or 2, m" is 0, or an integer having a value of 1 to 5;

v is 0, or an integer having a value of 1 or 2;

$R_2$ is hydrogen, $C(H)(A)(R_{22})$, $(CR_{10}R_{23})_nOR_9$, $(CR_{10}R_{23})_nOR_{11}$, $C_{1-10}$alkyl, halo-substituted $C_{1-10}$ alkyl, $C_{2-10}$ alkenyl, $C_{2-10}$ alkynyl, $C_{3-7}$ cycloalkyl, $C_{3-7}$cycloalkyl$C_{1-10}$ alkyl, $C_{5-7}$ cycloalkenyl, $C_{5-7}$ cycloalkenyl $C_{1-10}$alkyl, aryl, aryl$C_{1-10}$ alkyl, heteroaryl, heteroaryl$C_{1-10}$alkyl, heterocyclyl, heterocyclyl$C_{1-10}$ alkyl, $(CR_{10}R_{23})_nS(O)_mR_{18}$, $(CR_{10}R_{23})_nNHS(O)_2R_{18}$, $(CR_{10}R_{23})_nNR_{13}R_{14}$, $(CR_{10}R_{23})_nNO_2$, $(CR_{10}R_{23})_nCN$, $(CR_{10}R_{23})_nS(O)_mNR_{13}R_{14}$, $(CR_{10}R_{230})_nC(Z)R_{11}$, $(CR_{10}R_{23})_nOC(Z)R_{11}$, $(CR_{10}R_{23})_nC(Z)OR_{11}$, $(CR_{10}R_{23})_nC(Z)NR_{13}R_{14}$, $(CR_{10}R_{23})_nC(Z)NR_{11}OR_9$, $(CR_{10}R_{23})_nNR_{10}C(Z)R_{11}$, $(CR_{10}R_{23})_nNR_{10}C(Z)NR_{13}R_{14}$, $(CR_{10}R_{23})_nN(OR_6)C(Z)NR_{13}R_{14}$, $(CR_{10}R_{23})_nN(OR_6)C(Z)R_{11}$, $(CR_{10}R_{23})_nC(=NOR_6)R_{11}$, $(CR_{10}R_{23})_nNR_{10}C(=NR_{19})NR_{13}R_{14}$, $(CR_{10}R_{23})_nOC(Z)NR_{13}R_{14}$, $(CR_{10}R_{23})_nNR_{10}C(Z)NR_{13}R_{14}$, $(CR_{10}R_{23})_nNR_{10}C(Z)OR_{10}$, 5-$(R_{18})$-1,2,4-oxadizaol-3-yl or 4-$(R_{12})$-5-$(R_{18}R_{19})$-4,5-dihydro-1,2,4-oxadiazol-3-yl; wherein the cycloalkyl, cycloalkylalkyl, aryl, arylalkyl, heteroaryl, heteroarylalkyl, heterocyclic and heterocyclicalkyl groups may be optionally substituted;

A is an optionally substituted aryl, heterocyclyl, or heteroaryl ring, or A is a substituted $C_{1-10}$ alkyl;

$R_{22}$ is an optionally substituted $C_{1-10}$ alkyl;

$R_b$ is hydrogen, $C_{1-6}$ alkyl, $C_{3-7}$ cycloalkyl, aryl, aryl$C_{1-4}$ alkyl, heteroaryl, heteroaryl$C_{1-4}$alkyl, heterocyclyl, or heterocyclyl$C_{1-4}$ alkyl; and wherein each of these moieties may be optionally substituted;

$R_3$ is heterocyclyl, heterocyclyl$C_{1-10}$ alkyl or $R_8$;

$R_5$ is hydrogen, $C_{1-4}$ alkyl, $C_{2-4}$ alkenyl, $C_{2-4}$ alkynyl or $NR_7R_{17}$, excluding the moieties $SR_5$ being $SNR_7R_{17}$ and $SOR_5$ being SOH;

$R_6$ is hydrogen, a pharmaceutically acceptable cation, $C_{1-10}$ alkyl, $C_{3-7}$ cycloalkyl, aryl, aryl$C_{1-4}$ alkyl, heteroaryl, heteroaryl$C_{1-4}$ alkyl, heterocyclic, aroyl, or $C_{1-10}$ alkanoyl;

$R_7$ and $R_{17}$ is each independently selected from hydrogen or $C_{1-4}$ alkyl or $R_7$ and $R_{17}$ together with the nitrogen to which they are attached form a heterocyclic ring of 5 to 7 members which ring optionally contains an additional heteroatom selected from oxygen, sulfur or $NR_{15}$;

$R_8$ is $C_{1-10}$ alkyl, halo-substituted $C_{1-10}$ alkyl, $C_{2-10}$ alkenyl, $C_{2-10}$ alkynyl, $C_{3-7}$cycloalkyl, $C_{5-7}$ cycloalkenyl, aryl, aryl$C_{1-10}$ alkyl, heteroaryl, heteroaryl$C_{1-10}$ alkyl, $(CR_{10}R_{20})_nOR_{11}$, $(CR_{10}R_{20})_nS(O)_mR_{18}$, $(CR_{10}R_{20})_nNHS(O)_2R_{18}$, $(CR_{10}R_{20})_nNR_{13}R_{14}$; and wherein the aryl, arylalkyl, heteroaryl, and heteroarylalkyl moieties may be optionally substituted;

$R_9$ is hydrogen, $C(Z)R_{11}$ or optionally substituted $C_{1-10}$ alkyl, $S(O)_2R_{18}$, optionally substituted aryl or optionally substituted aryl-$C_{1-4}$ alkyl;

$R_{10}$ and $R_{20}$ are each independently selected from hydrogen or $C_{1-4}$ alkyl;

$R_{11}$ is hydrogen, $C_{1-10}$ alkyl, $C_{3-7}$ cycloalkyl, heterocyclyl, heterocyclyl $C_{1-10}$alkyl, aryl, aryl$C_{1-10}$ alkyl, heteroaryl or heteroaryl$C_{1-10}$ alkyl, wherein all of these moieties may be optionally substituted;

$R_{12}$ is hydrogen or $R_{16}$;

$R_{13}$ and $R_{14}$ is each independently selected from hydrogen or optionally substituted $C_{1-4}$ alkyl, optionally substituted aryl or optionally substituted aryl-$C_{1-4}$ alkyl, or together with the nitrogen which they are attached form a heterocyclic ring of 5 to 7 members which ring optionally contains an additional heteroatom selected from oxygen, sulfur or $NR_9$;

$R_{15}$ is $R_{10}$ or $C(Z)$-$C_{1-4}$ alkyl;

$R_{16}$ is $C_{1-4}$ alkyl, halo-substituted-$C_{1-4}$ alkyl, or $C_{3-7}$ cycloalkyl;

$R_{18}$ is $C_{1-10}$ alkyl, $C_{3-7}$ cycloalkyl, heterocyclyl, aryl, aryl$_{1-10}$alkyl, heterocyclyl, heterocyclyl-$C_{1-10}$alkyl, heteroaryl or heteroaryl$_{1-10}$alkyl;

$R_{19}$ is hydrogen, cyano, $C_{1-4}$ alkyl, $C_{3-7}$ cycloalkyl or aryl;

$R_{23}$ is hydrogen, $C_{1-6}$ alkyl, $C_{3-7}$ cycloalkyl, aryl, aryl$C_{1-4}$ alkyl, heteroaryl, heteroaryl$C_{1-4}$alkyl, heterocyclyl, or heterocyclyl$C_{1-4}$ alkyl moiety, all of which may be optionally substituted;

or a pharmaceutically acceptable salt thereof.

It is recognized that for compounds of Formula (I), (II) and (III), the $R_1$, $R_2$ and $R_4$ moieties are the same.

Suitable $R_1$ moieties for use herein include a 4-pyridyl, or 4-pyrimidinyl ring. More preferred is the 4-pyrimidinyl ring.

The $R_1$ moiety is optionally substituted one or more times, suitably 1 to 3 times, with Y, optionally substituted $C_{1-4}$ alkyl, halogen, hydroxyl, optionally substituted $C_{1-4}$alkylsulfinyl, $CH_2OR_{12}$, amino, mono and di-$C_{1-6}$ alkyl substituted amino, $N(R_{10})C(O)R_b$, $N(R_{10})S(O)_2R_d$, or an N-heterocyclyl ring which ring has from 5 to 7 members and optionally contains an additional heteroatom selected from oxygen, sulfur or $NR_{15}$.

Suitably Y is $X_1$-$R_a$; and $X_1$ is oxygen, sulfur or nitrogen, preferably oxygen.

Suitably $R_a$ is $C_{1-6}$alkyl, aryl, aryl$C_{1-6}$alkyl, heterocyclic, heterocyclyl$C_{1-6}$ alkyl, heteroaryl, or heteroaryl$C_{1-6}$alkyl, wherein each of these moieties may be optionally substituted as defined herein.

When $R_a$ is aryl, it is preferably phenyl or napthyl. When $R_a$ is arylalkyl, it is preferably benzyl or napthylmethyl. When $R_a$ is a heterocyclic or heterocyclic alkyl moiety, the heterocyclic portion is preferably pyrrolindinyl, piperidinyl, morpholino, tetrahydropyranyl, tetrahydrothiopyranyl, tetrahydrothipyransulfinyl, tetrahydrothio-pyransulfonyl, pyrrolindinyl, indole, or piperonyl ring. It is noted that the heterocyclic rings herein may contain unsaturation, such as in a tryptamine ring.

When $R_a$ is a heteroaryl ring as defined below, it is preferably a pyridine or tetrazole ring.

The $R_a$ aryl, heterocyclic and heteroaryl rings may be optionally substituted one or more times, preferably one to three times, independently with halogen; $C_{1-4}$ alkyl, such as methyl, ethyl, propyl, isopropyl, or t-butyl; halosubstituted alkyl, such as $CF_3$; hydroxy; hydroxy substituted $C_{1-4}$ alkyl; $(CR_{10}R_{20})_qC_{1-4}$ alkoxy, such as methoxy or ethoxy; $(CR_{10}R_{20})_qS(O)_m$alkyl and $(CR_{10}R_{20})_qS(O)_m$aryl (wherein m is 0, 1, or 2); $(CR_{10}R_{20})_qC(O)OR_{11}$, such as $C(O)C_{1-4}$ alkyl or $C(O)OH$ moieties; $(CR_{10}R_{20})_qC(O)R_{11}$; $(CR_{10}R_{20})_qOC(O)R_c$; $O—(CH_2)_s—O$; $(CR_{10}R_{20})_qNR_{13}R_{14}$; $(CR_{10}R_{20})_qN(R_{10})C(O)R_b$; $(CR_{10}R_{20})_qC(O)NR_{13}R_{14}$; $(CR_{10}R_{20})_qC(O)NR_{10}R_c$; $(CR_{10}R_{20})_qS(O)_2NR_{13}R_{14}$; $(CR_{10}R_{20})_qS(O)_2NR_{10}R_c$; $(CR_{10}R_{20})_qN(R_{10})S(O)_2R_c$; cyano, nitro, an N-heterocyclyl ring which ring has from 5 to 7 members and optionally contains an additional heteroatom selected from oxygen, sulfur or $NR_{15}$; aryl, such as phenyl; an optionally substituted arylalkyl, such as benzyl or phenethyl; aryloxy, such as phenoxy; or arylalkyloxy such as benzyloxy; and wherein the aryl, alkylalkyl, aryloxy and arylalkyloxy containing moieties may be optionally substituted themselves one to two times by halogen, hydroxy, hydroxy substituted alkyl, $C_{1-10}$ alkoxy, $S(O)_m$ alkyl, amino, $NR_7R_{17}$ group, $C_{1-4}$ alkyl, or halosubstituted $C_{1-4}$ alkyl.

Suitably, s is an integer having a value of 1, 2, or 3. Preferably s is 2 yielding a 1,3-dioxyethylene moiety, or ketal functionality.

Suitably, q is 0 or an integer having a value of 1 to 4.

Suitably, $R_b$ is hydrogen, $C_{1-6}$ alkyl, $C_{3-7}$ cycloalkyl, aryl, aryl$C_{1-4}$ alkyl, heteroaryl, heteroaryl$C_{1-4}$alkyl, heterocyclyl, or heterocyclyl$C_{1-4}$ alkyl moiety; all of which moieties may be optionally substituted as defined below.

Suitably, $R_c$ is an $C_{1-6}$ alkyl, $C_{3-7}$ cycloalkyl, aryl, aryl$C_{1-4}$ alkyl, heteroaryl, heteroaryl$C_{1-4}$alkyl, heterocyclyl, or heterocyclyl$C_{1-4}$ alkyl moiety, all of which moieties may be optionally substituted as defined below.

When the $R_a$ moiety is an alkyl group it may be optionally substituted as defined herein in the definition section below. Also, the alkyl portion of the $R_1$ substituents, where applicable, such as the mono- and di-$C_{1-6}$ alkyl amino moieties, may be halo substituted.

Preferred $R_a$ groups include, methyl, ethyl, benzyl, halo-substituted benzyl, napthylmethyl, phenyl, halosubstituted phenyl, aminocarbonylphenyl, alkylphenyl, cyanophenyl, alkylthiophenyl, hydroxyphenyl, alkoxyphenyl, phenoxyphenyl, benzyloxyphenyl, phenylphenyl, methylenedioxyphenyl, trifluoromethylphenyl, methylsulfonylphenyl, tetrazole, methyltetrazolyl, morpholinopropyl, piperonyl, piperidin-4-yl, alkyl substituted piperidine, such as 1-methyl piperidine, or 2,2,6,6-tetramethylpiperidin-4-yl.

Preferred ring substitution on the benzyl or phenyl rings is in the 4-position. Preferred substitution on the phenyl or phenyl alkyl groups is halogen, halosubstituted alkyl or alkyl groups, such as fluoro or chloro, or methyl.

When the additional $R_1$ optional substituent is $N(R_{10})C(O)R_b$, $R_b$ is preferably $C_{1-6}$ alkyl; preferably $R_{10}$ is hydrogen. It is also recognized that the $R_b$ moieties, in particular the $C_{1-6}$ alkyl group may be optionally substituted, preferably from one to three times, preferably with halogen, such as fluorine, as in trifluoromethyl or trifluroethyl.

The preferred ring placement for the optional substituents on the 4-pyridyl derivative is in the 2-position, and a preferred ring placement on the 4-pyrimidinyl ring is also at the 2-position. A preferred substituent group is methoxy.

Suitably, $R_4$ is a phenyl, naphth-1-yl, naphth-2-yl, or a heteroaryl ring, all of which rings may be optionally substituted, independently, by one or two substituents. More preferably $R_4$ is a phenyl or naphthyl ring.

Suitable substitutions for $R_4$ when this is a 4-phenyl, 4-naphth-1-yl, 5-naphth-2-yl or 6-naphth-2-yl moiety are one or two substituents each of which are independently selected from halogen, $SR_5$, $SOR_5$, $OR_{12}$, $CF_3$, or $(CR_{10}R_{20})_v NR_{10}R_{20}$, and for other positions of substitution on these rings preferred substitution is halogen, $S(O)_m R_3$, $OR_3$, $CF_3$, $(CR_{10}R_{20})_m NR_{13}R_{14}$, $NR_{10}C(Z)R_3$ and $NR_{10}S(O)_m R_8$.

When $R_4$ is a heteroaryl ring, the ring is substituted in a similar ring substitution pattern as for the phenyl ring as described above. Preferably, halogen, $SR_5$, $SOR_5$, $OR_{12}$, $CF_3$, or $(CR_{10}R_{20})_v NR_{10}R_{20}$.

Preferred substituents for the 4-position in phenyl and naphth-1-yl and on the 5-position in naphth-2-yl include halogen, especially fluoro and chloro and $SR_5$ and $SOR_5$ wherein $R_5$ is preferably a $C_{1-2}$ alkyl, more preferably methyl; of which the fluoro and chloro is more preferred, and most especially preferred is fluoro.

Preferred substituents for the 3-position in phenyl and naphth-1-yl rings include: halogen, especially fluoro and chloro; $OR_3$, especially $C_{1-4}$ alkoxy; $CF_3$, $NR_{10}R_{20}$, such as amino; $NR_{10}C(Z)R_3$, especially $NHCO(C_{1-10}$ alkyl); $NR_{10}S(O)_m R_8$, especially $NHSO_2(C_{1-10}$ alkyl), and $SR_3$ and $SOR_3$ wherein $R_3$ is preferably a $C_{1-2}$ alkyl, more preferably methyl. When the phenyl ring is disubstituted preferably it is two independent halogen moieties, such as fluoro and chloro, preferably di-chloro and more preferably in the 3,4-position. It is also preferred that for the 3-position of both the $OR_3$ and $ZC(Z)R_3$ moieties, $R_3$ may also include hydrogen.

Preferably, the $R_4$ moiety is an unsubstituted or substituted phenyl moiety. More preferably, $R_4$ is phenyl or phenyl substituted at the 4-position with fluoro and/or substituted at the 3-position with fluoro, chloro, $C_{1-4}$ alkoxy, methanesulfonamido or acetamido, or $R_4$ is a phenyl di-substituted at the 3,4-position independently with chloro or fluoro, more preferably chloro. Most preferably, $R_4$ is a 4-fluorophenyl.

Suitably, Z is oxygen or sulfur, preferably oxygen.

Suitably, $R_3$ is heterocyclyl, heterocyclyl$C_{1-10}$ alkyl or $R_8$.

Suitably, $R_5$ is hydrogen, $C_{1-4}$ alkyl, $C_{2-4}$ alkenyl, $C_{2-4}$ alkynyl or $NR_7R_{17}$, excluding the moieties $SR_5$ being $SNR_7R_{17}$ and $SOR_5$ being SOH.

Suitably, $R_6$ is hydrogen, a pharmaceutically acceptable cation, $C_{1-10}$ alkyl, $C_{3-7}$ cycloalkyl, aryl, aryl$C_{1-4}$ alkyl, heteroaryl, heteroaryl$C_{1-4}$alkyl, heterocyclyl, aroyl, or $C_{1-10}$ alkanoyl.

Suitably, $R_7$ and $R_{17}$ is each independently selected from hydrogen or $C_{1-4}$ alkyl or $R_7$ and $R_{17}$ together with the nitrogen to which they are attached form a heterocyclic ring of 5 to 7 members which ring optionally contains an additional heteroatom selected from oxygen, sulfur or $NR_{15}$.

Suitably, $R_8$ is $C_{1-10}$ alkyl, halo-substituted $C_{1-10}$ alkyl, $C_{2-10}$ alkenyl, $C_{2-10}$ alkynyl, $C_{3-7}$ cycloalkyl, $C_{5-7}$ cycloalkenyl, aryl, aryl$C_{1-10}$ alkyl, heteroaryl, heteroaryl $C_{1-10}$ alkyl, $(CR_{10}R_{20})_n OR_{11}$, $(CR_{10}R_{20})_n S(O)_m R_{18}$, $(CR_{10}R_{20})_n NHS(O)_2 R_{18}$, or $CR_{10}R_{20})_n NR_{13}R_{14}$; wherein the aryl, arylalkyl, heteroaryl, and heteroarylalkyl containing moieties may be optionally substituted.

Suitably, $R_9$ is hydrogen, $C(Z)R_{11}$, optionally substituted $C_{1-10}$ alkyl, $S(O)_2 R_{18}$, optionally substituted aryl or an optionally substituted aryl-$C_{1-4}$ alkyl.

Suitably, $R_{10}$ and $R_{20}$ are each independently selected from hydrogen or $C_{1-4}$ alkyl.

Suitably, $R_{11}$ is hydrogen, $C_{1-10}$ alkyl, $C_{3-7}$ cycloalkyl, heterocyclyl, heterocyclyl $C_{1-10}$alkyl, aryl, aryl$C_{1-10}$ alkyl, heteroaryl or heteroaryl$C_{1-10}$ alkyl; and wherein all of these moieties may be optionally substituted.

Suitably, $R_{12}$ is hydrogen or $R_{16}$; and $R_{16}$ is suitably, $C_{1-4}$ alkyl, halo-substituted-$C_{1-4}$ alkyl, or $C_{3-7}$ cycloalkyl.

Suitably, $R_{13}$ and $R_{14}$ is each independently selected from hydrogen or optionally substituted $C_{1-4}$ alkyl, optionally substituted aryl or optionally substituted aryl-$C_{1-4}$ alkyl, or together with the nitrogen which they are attached form a heterocyclic ring of 5 to 7 members which ring optionally contains an additional heteroatom selected from oxygen, sulfur or $NR_9$.

Suitably, $R_{15}$ is $R_{10}$ or $C(Z)$-$C_{1-4}$ alkyl.

Suitably, $R_{18}$ is $C_{1-10}$ alkyl, $C_{3-7}$ cycloalkyl, heterocyclyl, aryl, aryl$_{1-10}$alkyl, heterocyclyl, heterocyclyl-$C_{1-10}$alkyl, heteroaryl or heteroaryl$_{1-10}$alkyl.

Suitably, v is 0, or an integer having a value of 1 or 2.

Suitably, m is 0, or the integer 1 or 2.

Suitably, m' is an integer having a value of 1 or 2.

Suitably, m" is 0, or an integer having a value of 1 to 5.

Suitably, n is an integer having a value of 1 to 10.

Suitably, $R_2$ is hydrogen, $C(H)(A)(R_{22})$, $(CR_{10}R_{23})_n OR_9$, $(CR_{10}R_{23})_n OR_{11}$, $C_{1-10}$alkyl, halo-substituted $C_{1-10}$ alkyl, $C_{2-10}$ alkenyl, $C_{2-10}$ alkynyl, $C_{3-7}$ cycloalkyl, $C_{3-7}$cycloalkyl$C_{1-10}$ alkyl, $C_{5-7}$ cycloalkenyl, $C_{5-7}$ cycloalkenyl $C_{1-10}$alkyl, aryl, aryl$C_{1-10}$ alkyl, heteroaryl, heteroaryl$C_{1-10}$alkyl, heterocyclyl, heterocyclyl$C_{1-10}$ alkyl, $(CR_{10}R_{23})_n S(O)_m R_{18}$, $(CR_{10}R_{23})_n NHS(O)_2 R_{18}$, $(CR_{10}R_{23})_n NR_{13}R_{14}$, $(CR_{10}R_{23})_n NO_2$, $(CR_{10}R_{23})_n CN$, $(CR_{10}R_{23})_n S(O)_m NR_{13}R_{14}$, $(CR_{10}R_{230})_n C(Z)R_{11}$, $(CR_{10}R_{23})_n OC(Z)R_{11}$, $(CR_{10}R_{23})_n C(Z)OR_{11}$, $(CR_{10}R_{23})_n C(Z)NR_{13}R_{14}$, $(CR_{10}R_{23})_n C(Z)NR_{11}OR_9$, $(CR_{10}R_{23})_n NR_{10}C(Z)R_{11}$, $(CR_{10}R_{23})_nNR_{10}C(Z)NR_{13}R_{14}$, $(CR_{10}R_{23})_nN(OR_6)C(Z)NR_{13}R_{14}$, $(CR_{10}R_{23})_nN(OR_6)C(Z)R_{11}$, $(CR_{10}R_{23})_nC(=NOR_6)R_{11}$, $(CR_{10}R_{23})_nNR_{10}C(=NR_{19})NR_{13}R_{14}$, $(CR_{10}R_{23})_nOC(Z)NR_{13}R14$, $(CR_{10}R_{23})_nNR_{10}C(Z)NR_{13}R_{14}$, $(CR_{10}R_{23})_nNR_{10}C(Z)OR_{10}$, 5-$(R_{18})$-1,2,4-oxadizaol-3-yl or 4-$(R_{12})$-5-$(R_{18}R_{19})$-4,5-dihydro-1,2,4-oxadiazol-3-yl; wherein the cycloalkyl, cycloalkylalkyl, aryl, arylalkyl, heteroaryl, heteroaryl alkyl, heterocyclic and heterocyclic alkyl groups may be optionally substituted.

Suitably, $R_{23}$ is hydrogen, $C_{1-6}$ alkyl, $C_{3-7}$ cycloalkyl, aryl, aryl$C_{1-4}$ alkyl, heteroaryl, heteroaryl$C_{1-4}$alkyl, heterocyclyl, or a heterocyclyl$C_{1-4}$ alkyl moiety, all of which moieties may be optionally substituted as defined below.

Preferably, $R_2$ is hydrogen, $C(H)(A)(R_{22})$, an optionally substituted heterocyclyl ring, and optionally substituted heterocyclyl$C_{1-10}$ alkyl, an optionally substituted $C_{1-10}$ alkyl, an optionally substituted $C_{3-7}$cycloalkyl, an optionally substituted $C_{3-7}$cycloalkyl $C_{1-10}$ alkyl, $(CR_{10}R_{23})_nC(Z)OR_{11}$ group, $(CR_{10}R_{23})_nNR_{13}R_{14}$, $(CR_{10}R_{23})_nNHS(O)_2R_{18}$, $(CR_{10}R_{23})_nS(O)_mR_{18}$, an optionally substituted aryl; an optionally substituted aryl$C_{1-10}$ alkyl, $(CR_{10}R_{23})_nOR_{11}$, $(CR_{10}R_{23})_nC(Z)R_{11}$, or $(CR_{10}R_{23})_nC(=NOR_6)R_{11}$ group.

Suitably when $R_2$ is $C(H)(A)(R_{22})$ it is recognized that the first methylene carbon in this chain is a tertiary carbon, and it will contain one hydrogen moiety. This methylene group will have has two additional substituents, an $R_{22}$ moiety and an A moiety, i.e., $C(H)(A)(R_{22})$.

In a preferred embodiment, $R_2$ is a $C(AA_1)(A)$ moiety, wherein $AA_1$ is the $R_{22}$ moiety, but is specifically the side chain residue (R) of an amino acid, as is further described herein.

Suitably, A is an optionally substituted $C_{3-7}$cycloalkyl, aryl, heteroaryl, or heterocyclic ring, or A is a substituted $C_{1-10}$ alkyl moiety.

When A is an aryl, heteroaryl and heterocyclic ring, the ring may be substituted independently one or more times, preferably, 1 to 3 times by $C_{1-10}$ alkyl; halogen; halo substituted $C_{1-10}$ alkyl, such as $CF_3$; $(CR_{10}R_{20})_tOR_{11}$; $(CR_{10}R_{20})_tNR_{13}R_{14}$, especially amino or mono- or di-$C_{1-4}$ alkylamino; $(CR_{10}R_{20})_tS(O)_mR_{18}$ wherein m is 0, 1 or 2; SH; $NR_{10}C(Z)R_3$ (such $NHCO(C_{1-10}$ alkyl)); or $NR_{10}S(O)_mR_8$ (such as $NHSO_2(C_{1-10}$ alkyl)).

Suitably, t is 0, or an integer of 1 to 4.

When A is an optionally substituted cycloalkyl it is as defined below in the $R_{22}$ substitution.

When A is an optionally substituted heterocyclyl ring, the ring is preferably a morpholino, pyrrolidinyl, piperazinyl or a piperidinyl ring.

When A is an optionally substituted aryl moiety, it is preferably a phenyl ring.

When A is an optionally substituted heteroaryl ring, the heteroaryl term is as defined below in the definition section.

When A is a substituted $C_{1-10}$ alkyl moiety, the alkyl chain may be straight or branched. The chain is substituted independently 1 or more times, preferably 1 to 3 times by halogen, such as fluorine, chlorine, bromine or iodine; halosubstituted $C_{1-10}$ alkyl, such as $CF_3$; $C_{3-7}$cycloalkyl, $C_{1-10}$ alkoxy, such as methoxy or ethoxy; hydroxy substituted $C_{1-10}$ alkoxy; halosubstituted $C_{1-10}$ alkoxy, such as $OCF_2CF_2H$; $OR_{11}$; $S(O)_mR_{18}$ (wherein m is 0, 1 or 2); $NR_{13}R_{14}$; $C(Z)NR_{13}R_{14}$; $S(O)_mNR_{13}R_{14}$; $NR_{23}C(Z)R_{11}$; $NHS(O)_2R_{18}$; $C(Z)R_{11}$; $OC(Z)R_{11}$; $C(Z)OR_{11}$; $C(Z)NR_{11}OR_9$; $N(OR_6)C(Z)NR_{13}R_{14}$; $N(OR_6)C(Z)R_{11}$; $C(=NOR_6)R_{11}$; $NR_{23}C(=NR_{19})NR_{13}R_{14}$; $OC(Z)NR_{13}R_{14}$; $NR_{23}C(Z)NR_{13}R_{14}$; or $NR_{23}C(Z)OR_{10}$.

Preferably, A is a $C_{3-7}$ cycloalkyl, or a $C_{1-6}$ alkyl, more preferably a $C_{1-2}$ alkyl, i.e. a methylene or ethylene moiety, more preferably a methylene moiety which is substituted by one of the above noted groups.

Preferably, when A is an alkyl derivative, it is substituted by $OR_{11}$ where $R_{11}$ is preferably hydrogen, aryl or arylalkyl; $NR_{13}R_{14}$; $OC(Z)R11$; or $C(Z)OR_{11}$.

More preferably, A is substituted by $OR_{11}$ where $R_{11}$ is hydrogen.

Suitably, $R_{22}$ is a $C_{1-10}$ alkyl chain, which chain may be straight or branched and which may be optionally substituted independently, one or more times, preferably 1 to 3 times, by halogen, such as fluorine, chlorine, bromine or iodine; halo substituted $C_{1-10}$ alkyl; $C_{1-10}$ alkoxy, such as methoxy or ethoxy; hydroxy substituted $C_{1-10}$ alkoxy; halo-substituted $C_{1-10}$ alkoxy, such as $OCF_2CF_2H$; $OR_{11}$; $S(O)_mR_{18}$; $NR_{13}R_{14}$; $C(Z)NR_{13}R_{14}$; $S(O)_mNR_{13}R_{14}$; $NR_{23}C(Z)R_{11}$; $NHS(O)_2R_{18}$; $C(Z)R_{11}$; $OC(Z)R_{11}$; $C(Z)OR_{11}$; $C(Z)NR_{11}OR_9$; $N(OR_6)C(Z)NR_{13}R_{14}$; $N(OR_6)C(Z)R_{11}$; $C(=NOR_6)R_{11}$; $NR_{23}C(=NR_{19})NR_{13}R_{14}$; $OC(Z)NR_{13}R_{14}$; $NR_{23}C(Z)NR_{13}R_{14}$; $NR_{23}C(Z)OR_{10}$; optionally substituted $C_{3-7}$ cycloalkyl; optionally substituted aryl, such as phenyl; optionally substituted heteroaryl; or an optionally substituted heterocyclic moiety. The optional substituents on these cycloalkyl, aryl, heteroaryl, and heterocyclic moieties are as defined herein below.

It is noted that those $R_{22}$ substituent groups which contain carbon as the first connecting group, i.e. $C(Z)OR_{11}$; $C(Z)NR_{11}OR_9$, $C(Z)R_{11}$, $C(Z)NR_{13}R_{14}$, $C(=NOR_6)R_{11}$, may be the sole carbon in alkyl chain. Therefore, $R_{22}$ may, for instance, be a carboxy, an aldehyde, an amide, as well as being a substituent off a methylene unit, such as carbamoylmethyl, or acetamidomethyl. In other words, $R_{22}$ can be an optionally substituted alkyl group as defined above, or $R_{22}$ can be $C(Z)OR_{11}$, $C(Z)NR_{11}OR_9$, $C(Z)R_{11}$, $C(Z)NR_{13}R_{14}$, or $C(=NOR_6)R_{11}$. Preferably $R_{22}$ is a $C_{1-6}$ unsubstituted or substituted alkyl group, such as a $C_{1-3}$ alkylene, such as methyl, ethyl or isopropyl, or a methylene or ethylene moiety substituted by one of the above noted moieties, or as noted above those substituent groups which contain a carbon may substituent for the first methylene unit of the alkyl chain, such as carboxy, $C(O)OR_{11}$, $C(O)NR_{13}R_{14}$, or $R_{22}$ is an optionally substituted aryl group, such as a benzyl or phenethyl.

Preferably $R_{22}$ is a $C_{1-6}$ unsubstituted or substituted alkyl group, more preferably a $C_{1-2}$ alkylene chain, such as a methylene or ethylene moiety, more preferably methylene.

Preferably the $R_{22}$ alkyl chain is substituted by $OR_{11}$, where $R_{11}$ is preferably hydrogen, aryl or arylalkyl; $S(O)_mR_{18}$, where m is 0 and $R_{18}$ is a $C_{1-6}$ alkyl; or an optionally substituted aryl, i.e. a benzyl or phenethyl moiety.

More preferably, $R_{22}$ is methyl, phenyl, benzyl, $CH_2OH$, or $CH_2$—O-aryl.

Preferably, one or both of A and $R_{22}$ contain hydroxy moieties, such as in $C_{1-6}$ alkyl $OR_{11}$, wherein $R_{11}$ is hydrogen, i.e.$CH_2CH_2OH$.

Suitably, when $AA_1$ is the (R) side chain residue of an amino acid, it is a $C_{1-6}$ alkyl group, which may be straight or branched. This means the R group off the core amino acid of the structure R—C(H)(COOH)(NH$_2$). The R residue term is for example, $CH_3$ for alanine, $(CH_3)_2CH$— for valine, $(CH_3)_2CH$—$CH_2$— for leucine, phenyl-$CH_2$— for phenylalanine, $CH_3$—S—$CH_2$—$CH_2$— for methionine, etc. All generally recognized primary amino acids are included in this groups, such as but not limited to, alanine, arginine, asparagine, aspartic acid, cysteine, glutamine, glutamic acid, glycine, histidine, isoleucine, leucine, lysine, methionine, phenylalanine, serine, threonine, tryptophan, tyrosine, valine, hydroxylysine, methylhistidine, and other naturally occurring amino acids not found in proteins, such as b-alanine, g-aminobutyric acid, homocysteine, homoserine, citrulline, ornithine, canavanine, djenkolic acid, and b-cyanoalanine, or other naturally occurring non-mammalian amino acids.

Preferably $AA_1$ is the residue of phenylalanine, or alanine.

When $R_{22}$ is an optionally substituted heterocyclic moiety, the ring is preferably a morpholino, pyrrolidinyl, piperazinyl, or a piperidinyl group. When the heterocyclic ring is optionally substituted the substituents may be directly attached to the free nitrogen, such as in the piperidinyl group or pyrrole ring, or on the ring itself. Preferably the ring is a piperidine or pyrrole, more preferably piperidine.

The $R_{22}$ heterocyclyl ring may be optionally substituted one to four times independently by halogen; $C_{1-4}$ alkyl; aryl, such as phenyl; arylalkyl, such as benzyl, (and wherein the aryl or aryl alkyl moieties themselves may be optionally substituted as defined in the definition section below); $C(O)OR_{11}$, such as the $C(O)C_{1-4}$ alkyl or $C(O)OH$ moieties; $C(O)H$; $C(O)C_{1-4}$ alkyl; hydroxy substituted $C_{1-4}$ alkyl; $C_{1-4}$ alkoxy; $S(O)_m C_{1-4}$ alkyl (wherein m is 0, 1, or 2); or $NR_{10}R_{20}$ (wherein $R_{10}$ and $R_{20}$ are independently hydrogen or $C_{1-4}$alkyl).

Preferably if the ring is a piperidine, the substituents are attached directly on the available nitrogen, i.e. a 1-Formyl-4-piperidine, 1-benzyl-4-piperidine, 1-methyl-4-piperidine, 1-ethoxycarbonyl-4-piperidine. If the ring is substituted by an alkyl group and the ring is attached in the 4-position, it is preferably substituted in the 2- or 6-position or both, such as 2,2,6,6-tetramethyl-4-piperidine. Similarly, if the ring is a pyrrole, the substituents are all directly on the available nitrogen.

When the $R_{22}$ optional substituent is an optionally substituted aryl, it is preferably a phenyl; or when $R_{22}$ is an optionally substituted heteroaryl ring (as defined in the definition section below), the rings may be optionally substituted independently one or more times, preferably by one to three times by $C_{1-10}$ alkyl; halogen, especially fluoro or chloro; $(CR_{10}R_{20})_tOR_{11}$; $(CR_{10}R_{20})_tNR_{13}R_{14}$; especially amino or mono- or di-$C_{1-4}$ alkylamino; $(CR_{10}R_{20})_tS(O)_mR_{18}$, wherein m is 0, 1 or 2; SH; $OR_{11}$; $NR_{10}C(Z)R_3$ (such $NHCO(C_{1-10}$ alkyl)); or $NR_{10}S(O)_mR_8$ (such as $NHSO_2(C_{1-10}$ alkyl)).

When A or $R_{22}$ is an (optionally) substituted $C_{3-7}$cycloalkyl group, it is preferably a $C_3$ or $C_6$ ring, most preferably a $C_3$ ring, which ring may be optionally substituted one or more time, preferably 1 to 3 times, independently by halogen, such as fluorine, or chlorine; $(CR_{10}R_{20})_tOR_{11}$; $S(O)_mR_{18}$; cyano; $(CR_{10}R_{20})_tNR_{13}R_{14}$; especially amino or mono- or di-$C_{1-4}$ alkylamino; $N(R_{10})C(O)X_1$ and $X_1$ is $C_{1-4}$ alkyl, aryl or aryl$C_{1-4}$alkyl; $C_{1-10}$ alkyl, such as methyl, ethyl, propyl, isopropyl, or t-butyl; an optionally substituted alkyl wherein the substituents are halogen, (such as $CF_3$), hydroxy, nitro, cyano, amino, $NR_{13}R_{14}$, or $S(O)_mR_{18}$; an optionally substituted alkylene, such as ethylene or propylene; an optionally substituted alkyne, such as ethyne; $C(O)OR_{11}$; the group $R_e$; $C(O)H$; $=O$; $=N-OR_{11}$; $N(H)-OH$ (or substituted alkyl or aryl derivatives thereof on the nitrogen or the oxime moiety); or $N(OR_d)-C(O)-R_f$.

Suitably $R_d$ is hydrogen, a pharmaceutically acceptable cation, aroyl or a $C_{1-10}$ alkanoyl group.

Suitably $R_e$ is a 1,3-dioxyalkylene group of the formula $-O-(CH_2)_s-O-$, wherein s is 1 to 3, preferably s is 2 yielding a 1,3-dioxyethylene moiety, or ketal functionality.

Suitably $R_f$ is $NR_{21}R_{24}$; alkyl$_{1-6}$; halosubstituted alkyl$_{1-6}$; hydroxy substituted alkyl$_{1-6}$; alkenyl$_{2-6}$; aryl or heteroaryl optionally substituted by halogen, alkyl$_{1-6}$, halosubstituted alkyl$_{1-6}$, hydroxyl, or alkoxy$_{1-6}$.

Suitably $R_{21}$ is hydrogen, or alkyl$_{1-6}$.

Suitably $R_{24}$ is hydrogen, alkyl$_{1-6}$, aryl, benzyl, heteroaryl, alkyl substituted by halogen or hydroxyl, or phenyl substituted by a member selected from the group consisting of halo, cyano, alkyl$_{1-6}$, alkoxy$_{1-6}$, halosubstituted alkyl$_{1-6}$, $S(O)_m$alkyl$_{1-6}$; or $R_{21}$ and $R_{24}$ may together with the nitrogen to which they are attached form a ring having 5 to 7 members, which members may be optionally replaced by a heteroatom selected from oxygen, sulfur or nitrogen. The ring may be saturated or contain more than one unsaturated bond. Preferably $R_f$ is $NR_{21}R_{24}$, and more preferably $R_{21}$ and $R_{24}$ are both hydrogen.

When the A or $R_{22}$ optional substituent is $NR_{13}R_{14}$ it is recognized that in some instances this can yield the same moiety as a heterocyclic moiety noted above which is also a suitable variable. Preferably $R_{13}$ and $R_{14}$ are independently hydrogen, $C_{1-4}$ alkyl, preferably methyl, or benzyl.

When the A or $R_{22}$ optional substituent is a $C(Z)OR_{11}$ group, $R_{11}$ is suitably hydrogen, $C_{1-4}$ alkyl, especially methyl.

When the A or $R_{22}$ optional substituent is a $S(O)_mR_{18}$ group, $R_{18}$ is preferably aryl, especially phenyl, or a $C_{1-10}$ alkyl, especially methyl, or ethyl.

When the A or $R_{22}$ optional substituent is a $OR_{11}$ group, $R_{11}$ is preferably hydrogen, aryl, especially phenyl, or $C_{1-10}$ alkyl, especially methyl or ethyl.

When the A or $R_{22}$ optional substituent is a $NHS(O)_2R_{18}$ group, $R_{18}$ is suitably alkyl, especially methyl.

Preferably, $R_2$ is selected from hydrogen, $C(H)(A)(R_{22})$, $C_{1-10}$ alkyl, optionally substituted heterocyclyl, optionally substituted heterocyclyl$C_{1-10}$ alkyl, $(CR_{10}R_{23})_nNS(O)_2R_{18}$, $(CR_{10}R_{23})_nS(O)_mR_{18}$, aryl$C_{1-10}$ alkyl, $(CR_{10}R_{23})_nNR_{13}R_{14}$, optionally substituted $C_{3-7}$cycloalkyl, or optionally substituted $C_{3-7}$cycloalkyl $C_{1-10}$ alkyl.

When $R_2$ is an optionally substituted heterocyclyl, the ring is preferably a morpholino, pyrrolidinyl, piperazinyl, or a piperidinyl group. When the ring is optionally substituted, the substituents may be directly attached to the free nitrogen, such as in the piperidinyl group or pyrrole ring, or on the ring itself. Preferably the ring is a piperidine or pyrrole, more preferably piperidine. The heterocyclyl ring may be optionally substituted one to four times independently by halogen; $C_{1-4}$ alkyl; aryl, such as phenyl; aryl alkyl, such as benzyl—wherein the aryl or aryl alkyl moieties themselves may be optionally substituted (as in the definition section below); $C(O)OR_{11}$, such as the $C(O)C_{1-4}$ alkyl or $C(O)OH$ moieties; $C(O)H$; $C(O)C_{1-4}$ alkyl; hydroxy substituted $C_{1-4}$ alkyl; $C_{1-4}$ alkoxy; $S(O)_mC_{1-4}$ alkyl; or $NR_{10}R_{20}$.

Preferably if the ring is a piperidine, the substituents are directly attached on the available nitrogen, i.e. a 1-Formyl-4-piperidine, 1-benzyl-4-piperidine, 1-methyl-4-piperidine, 1-ethoxycarbonyl-4-piperidine. If the ring is substituted by an alkyl group and the ring is attached in the 4-position, it is preferably substituted in the 2- or 6-position or both, such as 2,2,6,6-tetramethyl-4-piperidine.

When $R_2$ is an optionally substituted heterocyclyl $C_{1-10}$ alkyl group, the ring is preferably a morpholino, pyrrolidinyl, piperazinyl or a piperidinyl group. Preferably the alkyl chain is 1 to 4 carbons, more preferably 3 or 4, and most preferably 3, such as in a propyl group. Preferred heterocyclic alkyl groups include but are not limited to, morpholino ethyl, morpholino propyl, pyrrolidinyl propyl, and piperidinyl propyl moieties.

When $R_2$ is an optionally substituted $C_{3-7}$cycloalkyl, or an optionally substituted $C_{3-7}$cycloalkyl $C_{1-10}$ alkyl, the cycloalkyl group is preferably a $C_3$ or $C_6$ ring, most preferably a $C_6$ ring, which rings may be optionally substituted. The cycloalkyl rings may be optionally substituted one to three times independently by halogen, such as fluorine, chlorine, bromine or iodine; hydroxy; $OC(O)R_b$, $C_{1-10}$ alkoxy, such as methoxy or ethoxy; $S(O)_m$ alkyl, such as methylthio, methylsulfinyl or methylsulfonyl; $S(O)_m$aryl; cyano, nitro; $NR_7R_{17}$; $N(R_{10})C(O)X_1$ and $X_1$ is $C_{1-4}$ alkyl, aryl or aryl$C_{1-4}$alkyl; $C_{1-10}$ alkyl, such as methyl, ethyl, propyl, isopropyl, or t-butyl; optionally substituted alkyl wherein the substituents are halogen, (such as $CF_3$), hydroxy, nitro, cyano, amino, $NR_7R_{17}$, $S(O)m$ alkyl and $S(O)m$ aryl; optionally substituted alkylene, such as ethylene or propylene; optionally substituted alkyne, such as ethyne; $C(O)OR_{11}$, such as the free acid or methyl ester derivative; the group $R_e$; $C(O)H$; $=O$; $=N-OR_{11}$; $N(H)-OH$ (or substituted alkyl or aryl derivatives thereof on the nitrogen or the oxime moiety); $N(OR_d)-C(O)-R_f$, an optionally substituted aryl, such as phenyl; an optionally substituted aryl$C_{1-4}$alkyl, such as benzyl or phenethyl; an optionally substituted heterocyclyl or heterocyclic $C_{1-4}$alkyl, and further wherein these aryl, arylalkyl, heterocyclic, and heterocyclic alkyl containing moieties are also optionally substituted one to two times by halogen, hydroxy, $C_{1-10}$ alkoxy, $S(O)_m$ alkyl, cyano, nitro, amino, mono & di-substituted $C_{1-6}$ amino, $C_{1-10}$ alkyl, or an halosubstituted $C_{1-10}$ alkyl.

$R_b$ is hydrogen, $C_{1-6}$ alkyl, $C_{3-7}$ cycloalkyl, aryl, aryl$C_{1-4}$ alkyl, heteroaryl, heteroaryl$C_{1-4}$alkyl, heterocyclyl, or heterocyclyl$C_{1-4}$ alkyl; and wherein each of these moieties may be optionally substituted.

$R_d$, $R_e$ and $R_f$ are as defined above.

When the $R_2$ cycloalkyl moiety is substituted by $NR_7R_{17}$ group, or $NR_7R_{17}$ $C_{1-10}$ alkyl group, and the $R_7$ and $R_{17}$ are as defined in Formula (I), the substituent is preferably an amino, amino alkyl, or an optionally substituted pyrrolidinyl moiety. In those cases where $NR_7R_{17}$ and $NR_{13}R_{14}$ together cyclize to form a 5 to 7 membered ring, it is noted that those rings may be optionally substituted 1 to 3 times as defined in the definition section.

A preferred subgenus of Formula (I) are the compounds of Formula (Ia) as represented by the general structure:

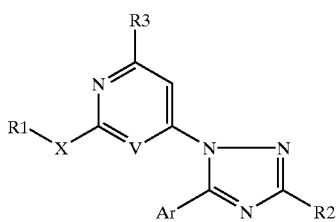

(Ia)

wherein X=O, NH, or S; V=CH, N; $R_3$ is an optional substituent on the $R_1$ moiety as defined in Formula (I); $R_1$ is $R_a$ as defined in Formula (I); Ar is $R_4$ as defined in Formula (I) and $R_2$ is as defined in Formula (I).

A preferred subgenus of Formula (II) are the compounds of Formula (IIa) represented by the general structure:

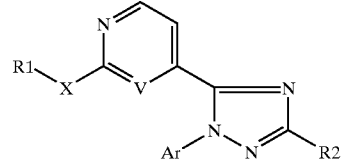

(IIa)

wherein X=O, NH, or S; V=CH, or N; $R_1$ is $R_a$ as defined in Formula (II); Ar is $R_4$ as defined in Formula (II) and $R_2$ is as defined in Formula (II).

A preferred subgenus of Formula (III) are compounds of Formula (IIIa) having the general structure:

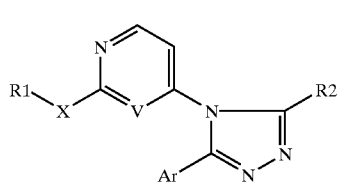

(IIIa)

wherein X=O, NH, or S; V=CH, or N; $R_1$ is $R_a$ as defined in Formula (III); Ar is $R_4$ as defined in Formula (III) and $R_2$ is as defined in Formula (III).

As used herein, "optionally substituted" unless specifically defined shall mean such groups as halogen, such as fluorine, chlorine, bromine or iodine; hydroxy; hydroxy substituted $C_{1-10}$alkyl; $C_{1-10}$ alkoxy, such as methoxy or ethoxy; halosubstituted $C_{1-10}$ alkoxy; $S(O)m$ alkyl, such as methyl thio, methylsulfinyl or methyl sulfonyl; $NR_7R_{17}$, such as amino or mono or -disubstituted $C_{1-4}$ alkyl or wherein the $R_7R_{17}$ can cyclize together with the nitrogen to which they are attached to form a 5 to 7 membered ring which optionally contains an additional heteroatom selected from O/N/S; $C_{1-10}$ alkyl, $C_{3-7}$cycloalkyl, or $C_{3-7}$cycloalkyl $C_{1-10}$ alkyl group, such as methyl, ethyl, propyl, isopropyl, t-butyl, etc. or cyclopropyl methyl; halosubstituted $C_{1-10}$ alkyl, such $CF_2CF_2H$, or $CF_3$; an optionally substituted aryl, such as phenyl, or an optionally substituted arylalkyl, such as benzyl or phenethyl, wherein these aryl containing moieties may also be substituted one to two times by halogen; hydroxy; hydroxy substituted alkyl; $C_{1-10}$ alkoxy; $S(O)_m$alkyl; amino, mono & di-substituted $C_{1-4}$ alkyl amino, such as in the $NR_7R_{17}$ group; $C_{1-4}$ alkyl, or $CF_3$.

Suitable pharmaceutically acceptable salts are well known to those skilled in the art and include basic salts of inorganic and organic acids, such as hydrochloric acid, hydrobromic acid, sulphuric acid, phosphoric acid, methane sulphonic acid, ethane sulphonic acid, acetic acid, malic acid, tartaric acid, citric acid, lactic acid, oxalic acid, succinic acid, fumaric acid, maleic acid, benzoic acid, salicylic acid, phenylacetic acid and mandelic acid.

In addition, pharmaceutically acceptable salts of compounds of Formula (I) may also be formed with a pharmaceutically acceptable cation, for instance, if a substituent group comprises a carboxy moiety. Suitable pharmaceutically acceptable cations are well known to those skilled in the art and include alkaline, alkaline earth, ammonium and quaternary ammonium cations.

The term "halo" or "halogens" is used herein to mean the halogens, chloro, fluoro, bromo and iodo.

The term "$C_{1-10}$alkyl" or "alkyl" or "alkyl$_{1-10}$" is used herein to mean both straight and branched chain radicals of 1 to 10 carbon atoms, unless the chain length is otherwise limited, including, but not limited to, methyl, ethyl, n-propyl, iso-propyl, n-butyl, sec-butyl, iso-butyl, tert-butyl, n-pentyl and the like.

The term "cycloalkyl" is used herein to mean cyclic radicals, preferably of 3 to 8 carbons, including but not limited to cyclopropyl, cyclopentyl, cyclohexyl, and the like.

The term "cycloalkenyl" is used herein to mean cyclic radicals, preferably of 5 to 8 carbons, which have at least one bond including but not limited to cyclopentenyl, cyclohexenyl, and the like.

The term "alkenyl" is used herein at all occurrences to mean straight or branched chain radical of 2–10 carbon atoms, unless the chain length is limited thereto, including, but not limited to ethenyl, 1-propenyl, 2-propenyl, 2-methyl-1-propenyl, 1-butenyl, 2-butenyl and the like.

The term "aryl" is used herein to mean phenyl and naphthyl.

The term "heteroaryl" (on its own or in any combination, such as "heteroaryloxy", or "heteroaryl alkyl") is used herein to mean a 5–10 membered aromatic ring system in which one or more rings contain one or more heteroatoms selected from the group consisting of N, O or S, such as, but not limited, to pyrrole, pyrazole, furan, thiophene, quinoline, isoquinoline, quinazolinyl, pyridine, pyrimidine, oxazole, thiazole, thiadiazole, tetrazole, triazole, imidazole, or benzimidazole.

The term "heterocyclic" (on its own or in any combination, such as "heterocyclylalkyl") is used herein to mean a saturated or partially unsaturated 4–10 membered ring system in which one or more rings contain one or more heteroatoms selected from the group consisting of N, O, or S; such as, but not limited to, pyrrolidine, piperidine, piperazine, morpholine, tetrahydropyran, or imidazolidine.

The term "aralkyl" or "heteroarylalkyl" or "heterocyclicalkyl" is used herein to mean $C_{1-4}$ alkyl as defined above attached to an aryl, heteroaryl or heterocyclic moiety as also defined herein unless otherwise indicate.

The term "sulfinyl" is used herein to mean the oxide S (O) of the corresponding sulfide, the term "thio" refers to the sulfide, and the term "sulfonyl" refers to the fully oxidized S $(O)_2$ moiety.

The term "aroyl" is used herein to mean C(O)Ar, wherein Ar is as phenyl, naphthyl, or aryl alkyl derivative such as defined above, such group include but are not limited to benzyl and phenethyl.

The term "alkanoyl" is used herein to mean $C(O)C_{1-10}$ alkyl wherein the alkyl is as defined above.

It is recognized that the compounds of the present invention may exist as stereoisomers, regioisomers, or diastereiomers. These compounds may contain one or more asymmetric carbon atoms and may exist in racemic and optically active forms. All of these compounds are included within the scope of the present invention.

Exemplified compounds of Formula (I), or pharmaceutically acceptable salts thereof, include:

1-(Pyrid-4yl)-3-phenyl-5-(4-fluorophenyl)-1,2,4-triazole;
1-(6-Aminopyrimidin-4yl)-3-phenyl-5-(4-fluorophenyl)-1,2,4-triazole;
1-[4-(6,7-Dimethoxyquinazoline)]-3-phenyl-5-(4-fluorophenyl)-1,2,4-triazole;

An exemplified compound of Formula (II), or a pharmaceutically acceptable salt thereof, is 1-(4-Fluorophenyl)-3-phenyl-5-(2-aminopyrimidin-4-yl)-1,2,4-triazole.

An exemplified compounds of Formula (III), ora pharmaceutically acceptable salt thereof, is:

3-(4-Fluorophenyl)-4-(2-aminopyrimidin-4-yl)-5-phenyl-1,2,4-triazole.

The compounds of Formula (I), (II) and (III) may be obtained by applying synthetic procedures, described herein. The synthesis provided for is applicable to producing compounds of Formula (I), (II) or (III) having a variety of different $R_1$, $R_2$, and $R_4$ groups which are reacted, employing optional substituents which are suitably protected, to achieve compatibility with the reactions outlined herein. Subsequent deprotection, in those cases, then affords compounds of the nature generally disclosed.

Once the triazole nucleus has been established, further compounds of Formula (I), (II) or (III) may be prepared by applying standard techniques for functional group interconversion, well known in the art. For instance: $C(O)NR_{13}R_{14}$ from $CO_2CH_3$ by heating with or without catalytic metal cyanide, e.g. NaCN, and $HNR_{13}R_{14}$ in $CH_3OH$; $OC(O)R_3$ from OH with e.g., $ClC(O)R_3$ in pyridine; $NR_{10}$—$C(S)NR_{13}R_{14}$ from $NHR_{10}$ with an alkylisothiocyante or thiocyanic acid; $NR_6C(O)OR_6$ from $NHR_6$ with the alkyl chloroformate; $NR_{10}C(O)NR_{13}R_{14}$ from $NHR_{10}$ by treatment with an isocyanate, e.g. HN=C=O or $R_{10}N$=C=O; $NR_{10}$—$C(O)R_8$ from $NHR_{10}$ by treatment with Cl—$C(O)R_3$ in pyridine; $C(=NR_{10})NR_{13}R_{14}$ from $C(NR_{13}R_{14})SR_3$ with $H_3NR_3{}^+OAc^-$ by heating in alcohol; $C(NR_{13}R_{14})SR_3$ from $C(S)NR_{13}R_{14}$ with $R_6$—I in an inert solvent, e.g. acetone; $C(S)NR_{13}R_{14}$ (where $R_{13}$ or $R_{14}$ is not hydrogen) from $C(S)NH_2$ with $HNR_{13}R_{14}$—$C(=NCN)$—$NR_{13}R_{14}$ from $C(=NR_{13}R_{14})$—$SR_3$ with $NH_2CN$ by heating in anhydrous alcohol, alternatively from $C(=NH)$—$NR_{13}R_{14}$ by treatment with BrCN and NaOEt in EtOH; $NR_{10}$—$C(=NCN)SR_8$ from $NHR_{10}$ by treatment with $(R_8S)_2C$=NCN; $NR_{10}SO_2R_3$ from $NHR_{10}$ by treatment with $ClSO_2R_3$ by heating in pyridine; $NR_{10}C(S)R_3$ from $NR_{10}C(O)R_8$ by treatment with Lawesson's reagent [2,4-bis(4-methoxyphenyl)-1,3,2,4-dithiadiphosphetane-2,4-disulfide]; $NR_{10}SO_2CF_3$ from $NHR_6$ with triflic anhydride and base wherein $R_3$, $R_6$, $R_{10}$, $R_{13}$ and $R_{14}$ are as defined in Formula (I) herein.

Precursors of the groups $R_1$, $R_2$ and $R_4$ can be other $R_1$, $R_2$ and $R_4$ groups which can be interconverted by applying standard techniques for functional group interconversion. For example a compound of the formula (I) wherein $R_2$ is halo substituted $C_{1-10}$ alkyl can be converted to the corresponding $C_{1-10}$ alkyl$N_3$ derivative by reacting with a suitable azide salt, and thereafter if desired can be reduced to the corresponding $C_{1-10}$alkyl$NH_2$ compound, which in turn can be reacted with $R_{18}S(0)_2X$ wherein X is halo (e.g., chloro) to yield the corresponding $C_{1-10}$alkylNHS$(0)_2R_{18}$ compound.

Alternatively a compound of the formula (I), (II) or (III) where $R_2$ is halo-substituted $C_{1-10}$-alkyl can be reacted with an amine $R_{13}R_{14}NH$ to yield the corresponding $C_{1-10}$-alkyl$NR_{13}R_{14}$ compound, or can be reacted with an alkali metal salt of $R_{18}SH$ to yield the corresponding $C_{1-10}$alkyl$SR_{18}$ compound.

A generally applicable synthesis of Formula (I) triazoles is outlined in Scheme 1 below which specifically illustrates the case for $R_2$=aryl, but which may be broadly applicable to all the $R_2$ groups of Formula (I). Condensation of a thioamide with an appropriately activated acyl compound, for example an acid chloride or mixed anhydride, either at low temperature or with heating as required in the presence of an appropriate base and solvent as required affords (1) (1-scheme-1). Imide (1) is further reacted with a heterocyclic hydrazine to produce the desired triazole (2) (2-scheme-1) as a final product or as is shown in scheme 1 as an intermediate. Further conversion of (2) through nucleophilc displacement of a leaving group alpha to the heterocyclic nitrogen, illustrated in Scheme 1 for chloride, produces (3) (3-scheme-1). Appropriate alpha leaving groups for the displacement are halides and sulfonate esters, such as trifates or mesylates and appropriate nucleophiles are may be either organic or inorganic oxygen, nitrogen or sulfur compounds. For example phenols, alcohols, primary or secondary amines, anilines and either alkyl or aryl sulfides which may be reacted as their metal salts or in the presence of an amine (such as triethylamine or DBU) or inorganic base (such as potassium carbonate) either with or without solvent and heated as required to effect the displacement.

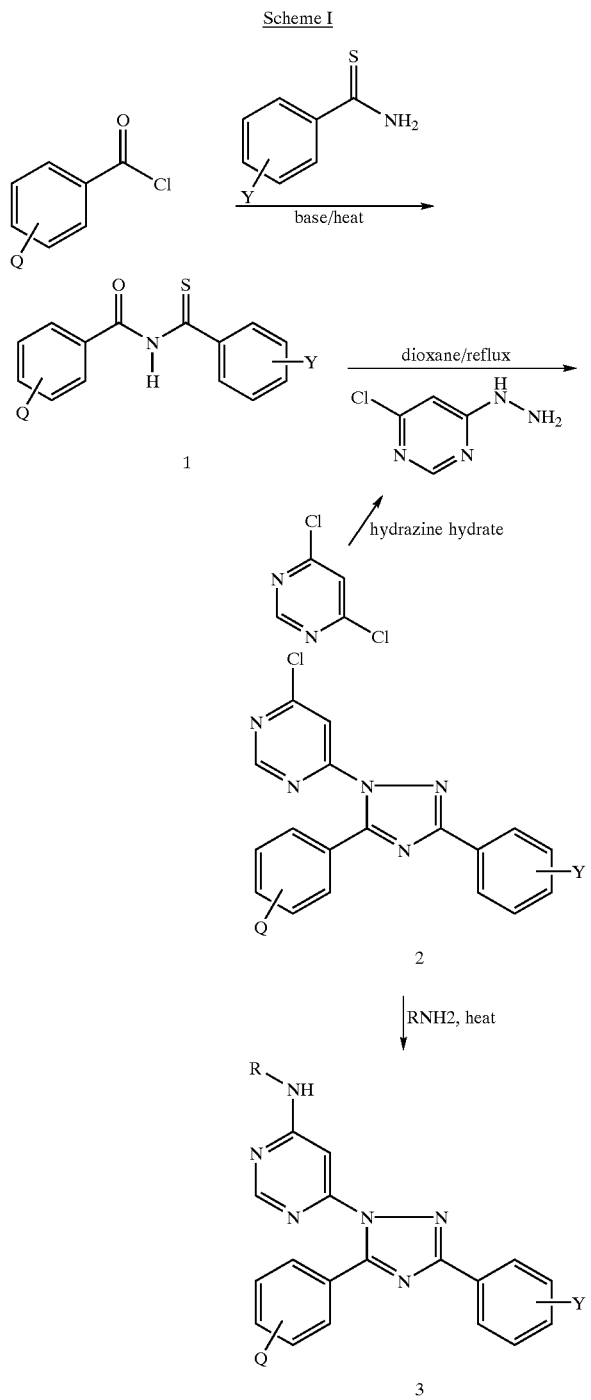

Compounds of the Formula (Ia) wherein V=CH, $R_3$=H, X=H can be prepared as described in Example 1b herein.

Compounds of the Formula (Ia) wherein V=N, R3=H, X=H can be prepared as described in Example 1b herein except by substituting pyrimidinyl-4-hydrazine (prepared in accordance with the procedures of Crooks et al., *Can. J. Chem.*, 1969, 47, 2061 whose disclosure is incorporated by reference herein in its entirety) for 4-pyridylhydrazine.

Compounds of Formula (Ia) wherein V=CH, $R_3$=H, X=O, NH, S can be prepared as described in Example 1b herein except by substituting 2-chloropyridyl-4-hydrazine (prepared in accordance with the procedures of Talik et al, *Rocz. Chem.*, 1955, 29, 1019 whose disclosure is incorporated by reference herein in its entirety) for 4-pyridylhydrazine, and carrying out the nucleophilic displacement of chloride ion as described in U.S. Pat. No. 5,670,527 example 35, and U.S. Pat. No. 5,658,903, example 27 whose disclosures are incorporated herein by reference in their entirety.

Compounds of the Formula (Ia) wherein V=N, R3=H, X=O, NH, S can be prepared as described in Example 1b herein by substituting 2-(methylthio)pyrimidine-4-hydrazine (prepared by heating 4-chloro-2-(methylthio) pyrimidine with hydrazine) for (4-pyridyl)hydrazine, and carrying out the oxidation/displacement protocol as described in U.S. Pat. No. 5,716,955 (Scheme II) whose disclosure is incorporated herein by reference in its entirety. The conditions for the displacement of alkyl sulfide or the sulfoxide or sulfone oxidation states thereof and the potential nucleophiles are the same as those described in Scheme I and are represented in Scheme II for $R_1X$ as defined in Formula (I).

Compounds of the Formula (Ia) wherein V=CH, R1=H, R3=H, X=O, NH, S and V=N, R1=H, R3=H, X=O, NH, S can be prepared such as described in U.S. Pat. No. 5,716,955 whose disclosure is incorporated herein by reference in its entirety.

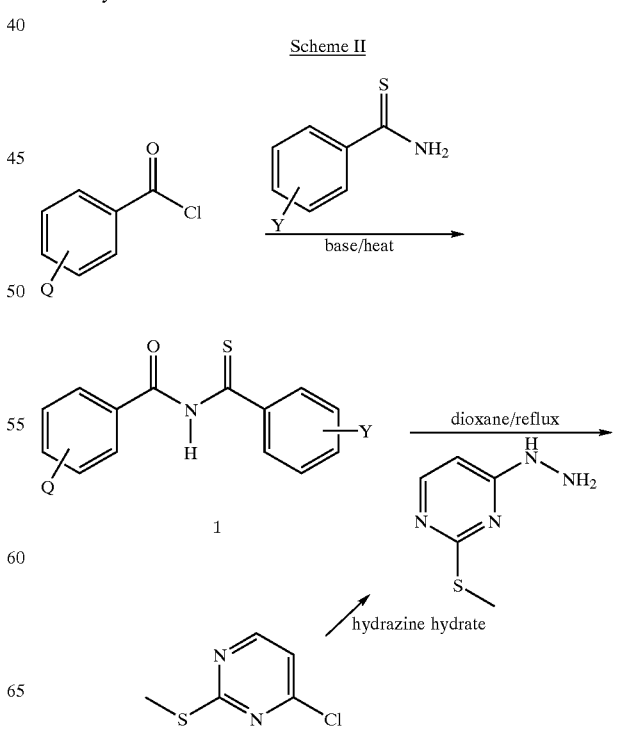

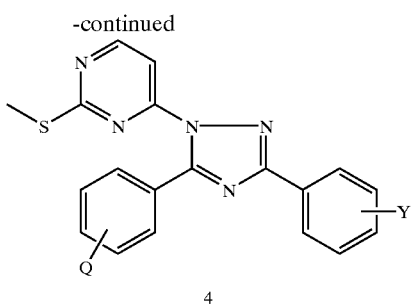

4

1.) oxidize
2.) RXH, heat

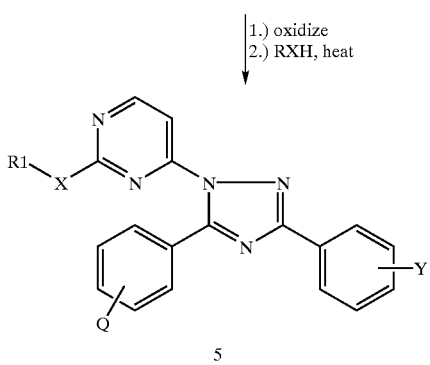

5

A generally applicable synthesis of Formula (II) triazoles is outlined in Scheme III below which specifically illustrates the case for R₁=substituted pyrimidine, but which may be broadly applicable to all the R₁ groups of Formula (II).

sure is incorporated herein by reference in its entirety) triazoles can be prepared by condensing the acyl chloride with thioamides to form the corresponding monothioimides. The monothioimides are then condensed with arylhydrazines to afford the 1,2,4-triazole nuclei. Displacement of the methylthio group (R₁—X not H) with nucleophiles (X=O, NH, S) can be effected by oxidation to the methylsulfinyl derivative with 3-chloroperoxybenzoic acid or oxone, followed by displacement with nucleophiles with or without the addition of bases such as sodium hydride, organolithiums or trialkylamines. In the case of amines (X=N), aluminum amide derivatives can be used to effect the displacements.

Compounds of Formula (IIa) wherein V=C, X=O, NH, S can be prepared as described above except substituting 2-chloropyridine-4-carboxylic acid for 2-(methylthio)pyrimidine-4-carboxylic, and carrying out the nucleophilic displacements of chloride ion according to the protocol described in U.S. Pat. No. 5,670,527 example 35, and U.S. Pat. No. 5,658,903; example 27 for 1-(4-piperidinyl)-4-(4-fluorophenyl)-5-(2-anilino-4-pyridinyl)imidazole whose disclosures are incorporated herein by reference in their entirety.

Compounds of the Formula (IIa) wherein V=CH, R1=H, X=O, NH, S and V=N, R1=H, X=O, NH, S can be prepared as described in U.S. Pat. No. 5,716,955 whose disclosure is incorporated by reference herein in its entirety.

A generally applicable synthesis of Formula (III) triazoles is outlined in Scheme IV below which specifically illustrates the case for R₁=substituted pyrimidine, but which may be broadly applicable to all the R₁ groups of Formula (III).

Scheme III

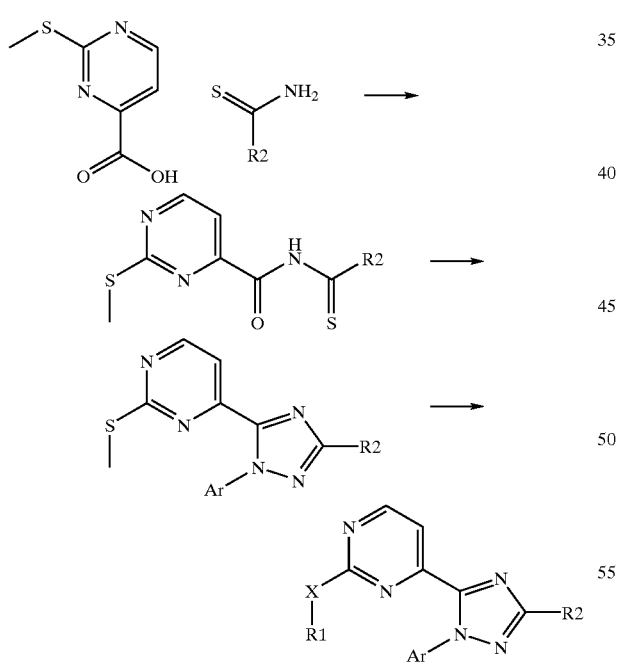

Scheme IV

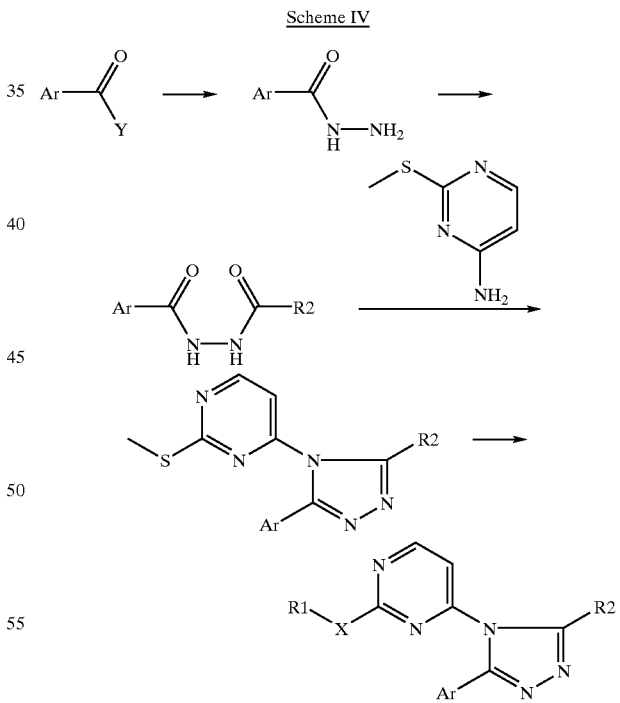

Compounds of Formula (IIa) wherein V=N, X=O, NH, or S can be prepared as shown in the scheme above. 2-(Methylthio)pyrimidine-4-carboxylic acid (prepared according to the method of Kim et al, *J. Med. Chem.,* 1986, 29, 1374 whose disclosure is incorporated herein by reference in its entirety) is converted to the acyl chloride (refluxing thionyl chloride). Following the procedure of Lin et al (*J. Heterocyclic Chem.,* 1983, 20, 1693 whose disclo- Compounds of Formula (III) wherein V=N, and X=O, NH, or S can be prepared as shown in the above scheme. Condensation of an activated ester with hydrazine yields the acylhydrazide, which upon treatment with a second activated ester, affords the 1,2-diacylhydrazide. Condensation with 4-amino-2-(methylthio)pyrimidine (prepared according to Brown et al, *J. Chem. Soc.,* 1962, 3172 whose disclosure is incorporated herein by reference in its entirety)

gives the triazole nucleus. Substitution of the methylthio group via an oxidation/displacement protocol as described for compounds of Formula (III) will allow one to access the 2-substituted pyrimidines.

Compounds of the Formula (IIIa) wherein V=CH, and X=O, N, or S can be prepared as described above except substituting 4-amino-2-chloropyridine for 4-amino-2-(methylthio)pyrimidine, and carrying out the nucleophilic displacements of chloride ion according to the protocol described in U.S. Pat. No. 5,670,527 example 35, and U.S. Pat. No. 5,658,903; example 27 for 1-(4-piperidinyl)-4-(4-fluorophenyl)-5-(2-anilino-4-pyridinyl)imidazole whose disclosures are incorporated herein by reference in their entirety.

Compounds of the Formula (IIIa) wherein V=CH, R1=H, X=O, NH, S and V=N, R1=H, X=O, NH, S can be prepared as described in U.S. Pat. No. 5,716,955 whose disclosure is incorporated herein by reference in its entirety.

Suitable protecting groups for use with hydroxyl groups and nitrogen groups are well known in the art and described in many references, for instance, Protecting Groups in Organic Synthesis, Greene T W, Wiley-Interscience, New York, 1981. Suitable examples of hydroxyl protecting groups include silyl ethers, such as t-butyldimethyl or t-butyldiphenyl, and alkyl ethers, such as methyl connected by an alkyl chain of variable link, $(CR_{10}R_{20})_n$.

Pharmaceutically acid addition salts of compounds of Formula (I) may be obtained in known manner, for example by treatment thereof with an appropriate amount of acid in the presence of a suitable solvent.

Methods of Treatment

The compounds of Formula (I) or a pharmaceutically acceptable salt thereof can be used in the manufacture of a medicament for the prophylactic or therapeutic treatment of any disease state in a human, or other mammal, which is exacerbated or caused by excessive or unregulated cytokine production by such mammal's cell, such as but not limited to monocytes and/or macrophages.

Compounds of Formula (I) are capable of inhibiting proinflammatory cytokines, such as IL-1, IL-6, IL-8, and TNF and are therefore of use in therapy. IL-1, IL-6, IL-8 and TNF affect a wide variety of cells and tissues and these cytokines, as well as other leukocyte-derived cytokines, are important and critical inflammatory mediators of a wide variety of disease states and conditions. The inhibition of these pro-inflammatory cytokines is of benefit in controlling, reducing and alleviating many of these disease states.

Accordingly, the present invention provides a method of treating a cytokine-mediated disease which comprises administering an effective cytokine-interfering amount of a compound of Formula (I) or a pharmaceutically acceptable salt thereof.

Compounds of Formula (I) are capable of inhibiting inducible proinflammatory proteins, such as COX-2, also referred to by many other names such as prostaglandin endoperoxide synthase-2 (PGHS-2) and are therefore of use in therapy. These proinflammatory lipid mediators of the cyclooxygenase (CO) pathway are produced by the inducible COX-2 enzyme. Regulation, therefore of COX-2 which is responsible for the these products derived from arachidonic acid, such as prostaglandins affect a wide variety of cells and tissues are important and critical inflammatory mediators of a wide variety of disease states and conditions. Expression of COX-1 is not effected by compounds of Formula (I). This selective inhibition of COX-2 may alleviate or spare ulcerogenic liability associated with inhibition of COX-1 thereby inhibiting prostoglandins essential for cytoprotective effects. Thus inhibition of these pro-inflammatory mediators is of benefit in controlling, reducing and alleviating many of these disease states. Most notably these inflammatory mediators, in particular prostaglandins, have been implicated in pain, such as in the sensitization of pain receptors, or edema. This aspect of pain management therefore includes treatment of neuromuscular pain, headache, cancer pain, and arthritis pain. Compounds of Formula (I) or a pharmaceutically acceptable salt thereof, are of use in the prophylaxis or therapy in a human, or other mammal, by inhibition of the synthesis of the COX-2 enzyme.

Accordingly, the present invention provides a method of inhibiting the synthesis of COX-2 which comprises administering an effective amount of a compound of Formula (I) or a pharmaceutically acceptable salt thereof. The present invention also provides for a method of prophylaxis treatment in a human, or other mammal, by inhibition of the synthesis of the COX-2 enzyme.

In particular, compounds of Formula (I) or a pharmaceutically acceptable salt thereof are of use in the prophylaxis or therapy of any disease state in a human, or other mammal, which is exacerbated by or caused by excessive or unregulated IL-1, IL-6, IL-8 or TNF production by such mammal's cell, such as, but not limited to, monocytes and/or macrophages.

Accordingly, in another aspect, this invention relates to a method of inhibiting the production of IL-1 in a mammal in need thereof which comprises administering to said mammal an effective amount of a compound of Formula (I) or a pharmaceutically acceptable salt thereof.

There are many disease states in which excessive or unregulated IL-1 production is implicated in exacerbating and/or causing the disease. These include rheumatoid arthritis, osteoarthritis, stroke, endotoxemia and/or toxic shock syndrome, other acute or chronic inflammatory disease states such as the inflammatory reaction induced by endotoxin or inflammatory bowel disease, tuberculosis, atherosclerosis, muscle degeneration, multiple sclerosis, cachexia, bone resorption, psoriatic arthritis, Reiter's syndrome, rheumatoid arthritis, gout, traumatic arthritis, rubella arthritis and acute synovitis. Recent evidence also links IL-1 activity to diabetes, pancreatic β cells disease, and Alzheimer's disease.

In a further aspect, this invention relates to a method of inhibiting the production of TNF in a mammal in need thereof which comprises administering to said mammal an effective amount of a compound of Formula (I) or a pharmaceutically acceptable salt thereof.

Excessive or unregulated TNF production has been implicated in mediating or exacerbating a number of diseases including rheumatoid arthritis, rheumatoid spondylitis, osteoarthritis, gouty arthritis and other arthritic conditions, sepsis, septic shock, endotoxic shock, gram negative sepsis, toxic shock syndrome, adult respiratory distress syndrome, stroke, cerebral malaria, chronic pulmonary inflammatory disease, silicosis, pulmonary sarcoisosis, bone resorption diseases, such as osteoporosis, reperfusion injury, graft vs. host reaction, allograft rejections, fever and myalgias due to infection, such as influenza, cachexia secondary to infection or malignancy, cachexia secondary to acquired immune deficiency syndrome (AIDS), AIDS, ARC (AIDS related complex), keloid formation, scar tissue formation, Crohn's disease, ulcerative colitis and pyresis.

Compounds of Formula (I) are also useful in the treatment of viral infections, where such viruses are sensitive to upregulation by TNF or will elicit TNF production in vivo.

The viruses contemplated for treatment herein are those that produce TNF as a result of infection, or those which are sensitive to inhibition, such as by decreased replication, directly or indirectly, by the TNF inhibiting-compounds of Formula (1). Such viruses include, but are not limited to HIV-1, HIV-2 and HIV-3, Cytomegalovirus (CMV), Influenza, adenovirus and the Herpes group of viruses, such as but not limited to, Herpes Zoster and Herpes Simplex. Accordingly, in a further aspect, this invention relates to a method of treating a mammal afflicted with a human immunodeficiency virus (HIV) which comprises administering to such mammal an effective TNF inhibiting amount of a compound of Formula (I) or a pharmaceutically acceptable salt thereof.

It is also recognized that both IL-6 and IL-8 are produced during rhinovirus (HRV) infections and contribute to the pathogenesis of common cold and exacerbation of asthma associated with HRV infection (Turner et al. (1998), Clin. Infec. Dis., Vol 26, p 840; Teren et al. (1997), Am J Respir Crit Care Med vol 155, p1362; Grunberg et al. (1997), Am J Respir Crit Care Med 156:609 and Zhu et al, J Clin Invest (1996), 97:421). It has also been demonstrated in vitro that infection of pulmonary epithelial cells with HRV results in production of IL-6 and IL-8 (Subauste et al., J. Clin. Invest. 1995, 96:549.) Epithelial cells represent the primary site of infection of HRV. Therefore another aspect of the present invention is a method of treatment to reduce inflammation associated with a rhinovirus infection, not necessarily a direct effect on virus itself.

Compounds of Formula (I) may also be used in association with the veterinary treatment of mammals, other than in humans, in need of inhibition of TNF production. TNF mediated diseases for treatment, therapeutically or prophylactically, in animals include disease states such as those noted above, but in particular viral infections. Examples of such viruses include, but are not limited to, lentivirus infections such as, equine infectious anaemia virus, caprine arthritis virus, visna virus, or maedi virus or retrovirus infections, such as but not limited to feline immunodeficiency virus (FIV), bovine immunodeficiency virus, or canine immunodeficiency virus or other retroviral infections.

The compounds of Formula (I) may also be used topically in the treatment or prophylaxis of topical disease states mediated by or exacerbated by excessive cytokine production, such as by IL-1 or TNF respectively, such as inflamed joints, eczema, psoriasis and other inflammatory skin conditions such as sunburn; inflammatory eye conditions including conjunctivitis; pyresis, pain and other conditions associated with inflammation.

Compounds of Formula (I) have also been shown to inhibit the production of IL-8 (Interleukin-8, NAP). Accordingly, in a further aspect, this invention relates to a method of inhibiting the production of IL-8 in a mammal in need thereof which comprises administering to said mammal an effective amount of a compound of Formula (I) or a pharmaceutically acceptable salt thereof.

There are many disease states in which excessive or unregulated IL-8 production is implicated in exacerbating and/or causing the disease. These diseases are characterized by massive neutrophil infiltration such as, psoriasis, inflammatory bowel disease, asthma, cardiac and renal reperfusion injury, adult respiratory distress syndrome, thrombosis and glomerulonephritis. All of these diseases are associated with increased IL-8 production which is responsible for the chemotaxis of neutrophils into the inflammatory site. In contrast to other inflammatory cytokines (IL-1, TNF, and IL-6), IL-8 has the unique property of promoting neutrophil chemotaxis and activation. Therefore, the inhibition of IL-8 production would lead to a direct reduction in the neutrophil infiltration.

The compounds of Formula (I) are administered in an amount sufficient to inhibit cytokine, in particular IL-1, IL-6, IL-8 or TNF, production such that it is regulated down to normal levels, or in some case to subnormal levels, so as to ameliorate or prevent the disease state. Abnormal levels of IL-1, IL-6, IL-8 or TNF, for instance in the context of the present invention, constitute: (i) levels of free (not cell bound) IL-1, IL-6, IL-8 or TNF greater than or equal to 1 picogram per ml; (ii) any cell associated IL-1, IL-6, IL-8 or TNF; or (iii) the presence of IL-1, IL-6, IL-8 or TNF mRNA above basal levels in cells or tissues in which IL-1, IL-6, IL-8 or TNF, respectively, is produced.

The discovery that the compounds of Formula (I) are inhibitors of cytokines, specifically IL-1, IL-6, IL-8 and TNF is based upon the effects of the compounds of Formulas (I) on the production of the IL-1, IL-8 and TNF in in vitro assays which are described herein.

As used herein, the term "inhibiting the production of IL-1 (IL-6, IL-8 or TNF)" refers to:

a) a decrease of excessive in vivo levels of the cytokine (IL-1, IL-6, IL-8 or TNF) in a human to normal or subnormal levels by inhibition of the in vivo release of the cytokine by all cells, including but not limited to monocytes or macrophages;

b) a down regulation, at the genomic level, of excessive in vivo levels of the cytokine (IL-1, IL-6, IL-8 or TNF) in a human to normal or sub-normal levels;

c) a down regulation, by inhibition of the direct synthesis of the cytokine (IL-1, IL-6, IL-8 or TNF) as a postranslational event; or d) a down regulation, at the translational level, of excessive in vivo levels of the cytokine (IL-1, IL-6, IL-8 or TNF) in a human to normal or sub-normal levels.

As used herein, the term "TNF mediated disease or disease state" refers to any and all disease states in which TNF plays a role, either by production of TNF itself, or by TNF causing another monokine to be released, such as but not limited to IL-1, IL-6 or IL-8. A disease state in which, for instance, IL-1 is a major component, and whose production or action, is exacerbated or secreted in response to TNF, would therefore be considered a disease stated mediated by TNF.

As used herein, the term "cytokine" refers to any secreted polypeptide that affects the functions of cells and is a molecule which modulates interactions between cells in the immune, inflammatory or hematopoietic response. A cytokine includes, but is not limited to, monokines and lymphokines, regardless of which cells produce them. For instance, a monokine is generally referred to as being produced and secreted by a mononuclear cell, such as a macrophage and/or monocyte. Many other cells however also produce monokines, such as natural killer cells, fibroblasts, basophils, neutrophils, endothelial cells, brain astrocytes, bone marrow stromal cells, epideral keratinocytes and B-lymphocytes. Lymphokines are generally referred to as being produced by lymphocyte cells. Examples of cytokines include, but are not limited to, Interleukin-1 (IL-1), Interleukin-6 (IL-6), Interleukin-8 (IL-8), Tumor Necrosis Factor-alpha (TNF-a) and Tumor Necrosis Factor beta (TNF-β).

As used herein, the term "cytokine interfering" or "cytokine suppressive amount" refers to an effective amount of a compound of Formula (I) which will cause a decrease in the in vivo levels of the cytokine to normal or sub-normal levels, when given to a patient for the prophylaxis or treatment of a disease state which is exacerbated by, or caused by, excessive or unregulated cytokine production.

As used herein, the cytokine referred to in the phrase "inhibition of a cytokine, for use in the treatment of a HIV-infected human" is a cytokine which is implicated in (a) the initiation and or maintenance of T cell activation and/or activated T cell-mediated HIV gene expression and/or replication and/or (b) any cytokine-mediated disease associated problem such as cachexia or muscle degeneration.

As TNF-β (also known as lymphotoxin) has close structural homology with TNF-a (also known as cachectin) and since each induces similar biologic responses and binds to the same cellular receptor, both TNF-a and TNF-β are inhibited by the compounds of the present invention and thus are herein referred to collectively as "TNF" unless specifically delineated otherwise.

A new member of the MAP kinase family, alternatively termed CSBP, p38, or RK, has been identified independently by several laboratories. Activation of this novel protein kinase via dual phosphorylation has been observed in different cell systems upon stimulation by a wide spectrum of stimuli, such as physicochemical stress and treatment with lipopolysaccharide or proinflammatory cytokines such as interleukin-1 and tumor necrosis factor. The cytokine biosynthesis inhibitors, of the present invention, compounds of Formula (I) have been determined to be potent and selective inhibitors of CSBP/p38/RK kinase activity. These inhibitors are of aid in determining the signaling pathways involvement in inflammatory responses. In particular, for the first time a definitive signal transduction pathway can be prescribed to the action of lipopolysaccharide in cytokine production in macrophages. In addition to those diseases already noted, treatment of stroke, neurotrauma, cardiac and renal reperfusion injury, congestive heart failure, chronic renal failure, angiogenesis & related processes, such as cancer, thrombosis, glomerulonephritis, diabetes and pancreatic b cells, multiple sclerosis, muscle degeneration, eczema, psoriasis, sunburn, and conjunctivitis are also included.

The CSBP inhibitors were subsequently tested in a number of animal models for anti-inflammatory activity. Model systems were chosen that were relatively insensitive to cyclooxygenase inhibitors in order to reveal the unique activities of cytokine suppressive agents. The inhibitors exhibited significant activity in many such in vivo studies. Most notable are its effectiveness in the collagen-induced arthritis model and inhibition of TNF production in the endotoxic shock model. In the latter study, the reduction in plasma level of TNF correlated with survival and protection from endotoxic shock related mortality. Also of great importance are the compounds effectiveness in inhibiting bone resorption in a rat fetal long bone organ culture system. Griswold et al., (1988) *Arthritis Rheum.* 31:1406–1412; Badger, et al., (1989) *Circ. Shock* 27, 51–61; Votta et al., (1994)in vitro. *Bone* 15, 533–538; Lee et al., (1993). *B Ann. N.Y. Acad. Sci.* 696, 149–170.

Chronic diseases which have an inappropriate angiogenic component are various ocular neovasularizations, such as diabetic retinopathy and macular degeneration. Other chronic diseases which have an excessive or increased proliferation of vasculature are tumor growth and metastasis, atherosclerosis, and certain arthritic conditions. Therefore CSBP kinase inhibitors will be of utility in the blocking of the angiogenic component of these disease states.

The term "excessive or increased proliferation of vasculature inappropriate angiogenesis" as used herein includes, but is not limited to, diseases which are characterized by hemangiomas and ocular diseases.

The term "inappropriate angiogenesis" as used herein includes, but is not limited to, diseases which are characterized by vesicle proliferation with accompanying tissue proliferation, such as occurs in cancer, metastasis, arthritis and atherosclerosis.

Accordingly, the present invention provides a method of treating a CSBP kinase mediated disease in a mammal in need thereof, preferably a human, which comprises administering to said mammal, an effective amount of a compound of Formula (I) or a pharmaceutically acceptable salt thereof.

In order to use a compound of Formula (I) or a pharmaceutically acceptable salt thereof in therapy, it will normally be formulated into a pharmaceutical composition in accordance with standard pharmaceutical practice. This invention, therefore, also relates to a pharmaceutical composition comprising an effective, non-toxic amount of a compound of Formula (I) and a pharmaceutically acceptable carrier or diluent.

Compounds of Formula (I), pharmaceutically acceptable salts thereof and pharmaceutical compositions incorporating such may conveniently be administered by any of the routes conventionally used for drug administration, for instance, orally, topically, parenterally or by inhalation. The compounds of Formula (I) may be administered in conventional dosage forms prepared by combining a compound of Formula (I) with standard pharmaceutical carriers according to conventional procedures. The compounds of Formula (I) may also be administered in conventional dosages in combination with a known, second therapeutically active compound. These procedures may involve mixing, granulating and compressing or dissolving the ingredients as appropriate to the desired preparation. It will be appreciated that the form and character of the pharmaceutically acceptable character or diluent is dictated by the amount of active ingredient with which it is to be combined, the route of administration and other well-known variables. The carrier(s) must be "acceptable" in the sense of being compatible with the other ingredients of the formulation and not deleterious to the recipient thereof.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time delay material well known to the art, such as glyceryl mono-stearate or glyceryl distearate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg. to about 1 g. When a liquid carrier is used, the preparation will be in the form of a syrup, emulsion, soft gelatin capsule, sterile injectable liquid such as an ampule or nonaqueous liquid suspension.

Compounds of Formula (I) may be administered topically, that is by non-systemic administration. This includes the application of a compound of Formula (I) externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as liniments, lotions, creams, ointments or pastes, and drops suitable for administration to the eye, ear or nose. The active ingredient may comprise, for topical administration, from 0.001% to 10% w/w, for instance from 1% to 2% by weight of the formulation. It may however comprise as much as 10% w/w but preferably will comprise less than 5% w/w, more preferably from 0.1% to 1% w/w of the formulation.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives or a fatty acid such as steric or oleic acid together with an alcohol such as propylene glycol or a macrogel. The formulation may incorporate any suitable surface active agent such as an anionic, cationic or non-ionic surfactant such as a sorbitan ester or a polyoxyethylene derivative thereof. Suspending agents such as natural gums, cellulose derivatives or inorganic materials such as silicaceous silicas, and other ingredients such as lanolin, may also be included.

Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified by filtration, transferred to a suitable container which is then sealed and sterilized by autoclaving or maintaining at 98–100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Compounds of Formula (I) may be administered parenterally, that is by intravenous, intramuscular, subcutaneous intranasal, intrarectal, intravaginal or intraperitoneal administration. The subcutaneous and intramuscular forms of parenteral administration are generally preferred. Appropriate dosage forms for such administration may be prepared by conventional techniques. Compounds of Formula (I) may also be administered by inhalation, that is by intranasal and oral inhalation administration. Appropriate dosage forms for such administration, such as an aerosol formulation or a metered dose inhaler, may be prepared by conventional techniques.

For all methods of use disclosed herein for the compounds of Formula (I), the daily oral dosage regimen will preferably be from about 0.1 to about 80 mg/kg of total body weight, preferably from about 0.2 to 30 mg/kg, more preferably from about 0.5 mg to 15 mg. The daily parenteral dosage regimen about 0.1 to about 80 mg/kg of total body weight, preferably from about 0.2 to about 30 mg/kg, and more preferably from about 0.5 mg to 15 mg/kg. The daily topical dosage regimen will preferably be from 0.1 mg to 150 mg, administered one to four, preferably two or three times daily. The daily inhalation dosage regimen will preferably be from about 0.01 mg/kg to about 1 mg/kg per day. It will also be recognized by one of skill in the art that the optimal quantity and spacing of individual dosages of a compound of Formula (I) or a pharmaceutically acceptable salt thereof will be determined by the nature and extent of the condition being treated, the form, route and site of administration, and the particular patient being treated, and that such optimums can be determined by conventional techniques. It will also be appreciated by one of skill in the art that the optimal course of treatment, i.e., the number of doses of a compound of Formula (I) or a pharmaceutically acceptable salt thereof given per day for a defined number of days, can be ascertained by those skilled in the art using conventional course of treatment determination tests.

The novel compounds of Formula (I) may also be used in association with the veterinary treatment of mammals, other than humans, in need of inhibition of CSBP/p38 or cytokine inhibition or production. In particular, CSBP/p38 mediated diseases for treatment, therapeutically or prophylactically, in animals include disease states such as those noted herein in the Methods of Treatment section, but in particular viral infections. Examples of such viruses include, but are not limited to, lentivirus infections such as, equine infectious anaemia virus, caprine arthritis virus, visna virus, or maedi virus or retrovirus infections, such as but not limited to feline immunodeficiency virus (FIV), bovine immunodeficiency virus, or canine immunodeficiency virus or other retroviral infections.

The invention will now be described by reference to the following biological examples which are merely illustrative and are not to be construed as a limitation of the scope of the present invention.

Biological Examples

The cytokine-inhibiting effects of compounds of the present invention may be determined by the following in vitro assays:

Assays for Interleukin-1 (IL-1), Interleukin-8 (IL-8), and Tumour Necrosis Factor (TNF) are well known in the art, and may be found in a number of publications, and patents. Representative suitable assays for use herein are described in Adams et al., U.S. Pat. No. 5,593,992, whose disclosure is incorporated by reference in its entirety.

Interleukin-1 (IL-1)

Human peripheral blood monocytes are isolated and purified from either fresh blood preparations from volunteer donors, or from blood bank buffy coats, according to the procedure of Colotta et al, J Immunol, 132, 936 (1984). These monocytes ($1 \times 10^6$) are plated in 24-well plates at a concentration of 1–2 million/ml per well. The cells are allowed to adhere for 2 hours, after which time non-adherent cells are removed by gentle washing. Test compounds are then added to the cells for 1 h before the addition of lipopolysaccharide (50 ng/ml), and the cultures are incubated at 37° C. for an additional 24 h. At the end of this period, culture supernatants are removed and clarified of cells and all debris. Culture supernatants are then immediately assayed for IL-1 biological activity, either by the method of Simon et al. J. Immunol. Methods, 84, 85, (1985) (based on ability of IL-1 to stimulate a Interleukin 2 producing cell line (EL-4) to secrete IL-2, in concert with A23187 ionophore) or the method of Lee et al., J. ImmunoTherapy, 6 (1), 1–12 (1990) (ELISA assay).

Compounds of Formula (I), exemplified by Example 1, were found to be active in this assay having an IC50 of <7 uM.

In vivo TNF Assay (1) Griswold et al., *Drugs Under Exp. and Clinical Res.*, *XIX* (6), 243–248 (1993); or (2) Boehm, et al., *Journal Of Medicinal Chemistry* 39, 3929–3937 (1996) whose disclosures are incorporated by reference herein in their entirety.

LPS-induced TNFα Production in Mice and Rats

In order to evaluate in vivo inhibition of LPS-induced TNFα production in rodents, both mice and rats are injected with LPS.

Mouse Method

Male Balb/c mice from Charles River Laboratories are pretreated (30 minutes) with compound or vehicle. After the 30 min. pretreat time, the mice are given LPS (lipopolysaccharide from *Esherichia coli* Serotype 055–85, Sigma Chemical Co., St Louis, Mo.) 25 ug/mouse in 25 ul phosphate buffered saline (pH 7.0) intraperitoneally. Two hours later the mice are killed by $CO_2$ inhalation and blood samples are collected by exsanguination into heparinized blood collection tubes and stored on ice. The blood samples are centrifuged and the plasma collected and stored at −20° C. until assayed for TNFα by ELISA.

Rat Method

Male Lewis rats from Charles River Laboratories are pretreated at various times with compound or vehicle. After a determined pretreat time, the rats are given LPS (lipopolysaccharide from *Esherichia coli* Serotype 055–85, Sigma Chemical Co., St Louis, Mo.) 3.0 mg/kg intraperitoneally. The rats are killed by $CO_2$ inhalation and heparinized whole blood is collected from each rat by cardiac puncture 90 minutes after the LPS injection. The blood samples are centrifuged and the plasma collected for analysis by ELISA for TNFα levels.

ELISA Method

TNFα levels were measured using a sandwich ELISA, as described in Olivera et al., Circ. Shock, 37, 301–306, (1992), whose disclosure is incorporated by reference in its entirety herein, using a hamster monoclonal antimurine TNFα (Genzyme, Boston, Mass.) as the capture antibody and a polyclonal rabbit antimurine TNFα (Genzyme) as the second antibody. For detection, a peroxidase-conjugated goat antirabbit antibody (Pierce, Rockford, Ill.) was added, followed by a substrate for peroxidase (1 mg/ml orthophenylenediamine with 1% urea peroxide). TNFα levels in the plasma samples from each animal were calculated from a standard curve generated with recombinant murine TNFα (Genzyme).

LPS-Stimulated Cytokine Production in Human Whole Blood Assay

Test compound concentrations were prepared at 10× concentrations and LPS prepared at 1 ug/ml (final conc. of 50 ng/ml LPS) and added in 50 uL volumes to 1.5 mL eppendorf tubes. Heparinized human whole blood was obtained from healthy volunteers and was dispensed into eppendorf tubes containing compounds and LPS in 0.4 mL volumes and the tubes incubated at 37 C. Following a 4 hour incubation, the tubes were centrifuged at 5000 rpm for 5 minutes in a TOMY microfuge, plasma was withdrawn and frozen at −80 C.

Cytokine Measurement

IL-1 and/or TNF were quantified using a standardized ELISA technology. An in-house ELISA kit was used to detect human IL-1 and TNF. Concentrations of IL-1 or TNF were determined from standard curves of the appropriate cytokine and IC50 values for test compound (concentration that inhibited 50% of LPS-stimulated cytokine production) were calculated by linear regression analysis.

CSBP/p38 Kinase Assay

This assay measures the CSBP/p38-catalyzed transfer of $^{32}P$ from [a-$^{32}P$]ATP to threonine residue in an epidermal growth factor receptor (EGFR)-derived peptide (T669) with the following sequence: KRELVEPLTPSGEAPNQALLR (residues 661–681). (See Gallagher et al., "Regulation of Stress Induced Cytokine Production by Pyridinyl Imidazoles: Inhibition of CSBP Kinase", BioOrganic & Medicinal Chemistry, 1997, 5, 49–64).

Reactions were carried in round bottom 96 well plate (from Coming) in a 30 ml volume. Reactions contained (in final concentration): 25 mM Hepes, pH 7.5; 8 mM $MgCl_2$; 0.17 mM ATP (the $Km_{[ATP]}$ of p38 (see Lee et al., Nature 300, n72 pg. 639–746 (December 1994)); 2.5 uCi of [g-32P] ATP; 0.2 mM sodium orthovanadate; 1 mM DTT; 0.1% BSA; 10% glycerol; 0.67 mM T669 peptide; and 2–4 nM of yeast-expressed, activated and purified p38. Reactions were initiated by the addition of [gamma-32P]Mg/ATP, and incubated for 25 min. at 37° C. Inhibitors (dissolved in DMSO) were incubated with the reaction mixture on ice for 30 minutes prior to adding the 32P-ATP. Final DMSO concentration was 0.16%. Reactions were terminated by adding 10 ul of 0.3 M phosphoric acid, and phosphorylated peptide was isolated from the reactions by capturing it on p81 phosphocellulose filters. Filters were washed with 75 mM phosphoric acids, and incorporated 32P was quantified using beta scintillation counter. Under these conditions, the specific activity of p38 was 400–450 pmol/pmol enzyme, and the activity was linear for up to 2 hr of incubation. The kinase activity values were obtained after subtracting values generated in the absence of substrate which were 10–15% of total values.

Representative final compounds of Formula (I), Example 2 demonstrated positive inhibitory activity of an $IC_{50}$ of <50 uM in this binding assay or a similar assay. Example 3 was found not to be active in this binding assay at concentrations of 100 uM.

Prostoglandin Endoperoxide Synthase-2 (PGHS-2) Assay

This assay describes a method for determining the inhibitory effects of compounds of Formula (I) on human PGHS-2 protein expression in LPS stimulated human monocytes. A suitable assay for PGHS-2 protein expression may be found in a number of publications, including U.S. Pat. No. 5,593, 992 whose disclosure is incorporated herein by reference.

TNF-a in Traumatic Brain Injury Assay

This assay provides for examination of the expression of tumor necrosis factor mRNA in specific brain regions which follow experimentally induced lateral fluid-percussion traumatic brain injury (TBI) in rats. Since TNF-a is able to induce nerve growth factor (NGF) and stimulate the release of other cytokines from activated astrocytes, this post-traumatic alteration in gene expression of TNF-a plays an important role in both the acute and regenerative response to CNS trauma. A suitable assay may be found in WO 97/35856 whose disclosure is incorporated herein by reference.

CNS Injury model for IL-b mRNA

This assay characterizes the regional expression of interleukin-1 B (IL-1β) mRNA in specific brain regions following experimental lateral fluid-percussion traumatic brain injury (TBI) in rats. Results from these assays indicate that following TBI, the temporal expression of IL-1β mRNA is regionally stimulated in specific brain regions. These regional changes in cytokines, such as IL-1β play a role in the post-traumatic pathologic or regenerative sequelae of brain injury. A suitable assay may be found in WO 97/35856 whose disclosure is incorporated herein by reference.

Angiogenesis Assay

Described in WO 97/32583, whose disclosure is incorporated herein by reference, is an assay for determination of inflammatory angiogenesis which may be used to show that cytokine inhibition will stop the tissue destruction of excessive or inappropriate proliferation of blood vessels.

SYNTHETIC EXAMPLES

The invention will now be described by reference to the following examples which are merely illustrative and are not to be construed as a limitation of the scope of the present invention. All temperatures are given in degrees centigrade, all solvents are highest available purity and all reactions run under anhydrous conditions in an argon atmosphere unless otherwise indicated.

In the Examples, all temperatures are in degrees Centigrade (° C.). Mass spectra were performed upon a VG Zab mass spectrometer using fast atom bombardment or on a micromass platform electrospray ionization mass spectrometer in the positive ion mode using 95:5 $CH_3CN/CH_3OH$ with 1% formic acid as the carrier solvent, unless otherwise indicated. $^1$H-NMR (hereinafter "NMR") spectra were recorded at 250 MHz using a Bruker AM 250 or Am 400 spectrometer. Multiplicities indicated are: s=singlet, d=doublet, t=triplet, q=quartet, m=multiplet and br indicates a broad signal. Sat. indicates a saturated solution, eq indicates the proportion of a molar equivalent of reagent relative to the principal reactant.

Flash chromatography is run over Merck Silica gel 60 (230 –400 mesh).

Example 1

1-(Pyrid-4-yl)-3-phenyl-5-(4-fluorophenyl)-1,2,4-triazole

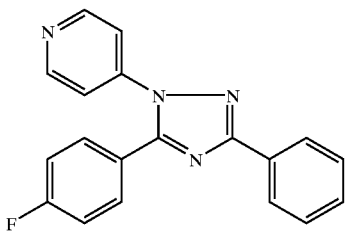

a) N-(4-Fluorobenzoyl)thiobenzamide

To a solution of 4-fluorobenzoylchloride (1.3 g, 8.5 mmol) in acetone (7.0 ml) was added a solution of thiobenzamide (1.16 g, 8.5 mmol) and pyridine (0.66 g, 8.5 mmol) in acetone (7.0 ml). The mixture was refluxed for 6 h. and cooled to room temperature. The reaction mixture was poured into water/ice and extracted with chloroform. Flash chromatography on silica gel afforded 0.5 g of the title compound as a red solid.

b) 1-(Pyrid-4-yl)-3-phenyl-5-(4-fluorophenyl)-1,2,4-triazole

To a solution of N-(4-fluorobenzoyl)thiobenzamide (0.5 g, 1.9 mmol), (4-pyridyl)hydrazine hydrochloride (0.336 g, 2.3 mmol) and sodium acetate (0.19 g, 2.3 mmol) in acetic acid/dioxane (6 ml/1:1) was stirred at 90° C. for 24 h. The reaction mixture was cooled and evaporated in vacuo. The residue was purified by flash chromatography on silica gel. Elution with ethylacetate/hexane (1:4) and subsequent crystallization afforded the triazole as a white solid. m.p. 134–135 C.

Example 2

1-(6-Aminopyrimidin-4-yl)-3-phenyl-5-(4-fluorophenyl)-1,2,4-triazole

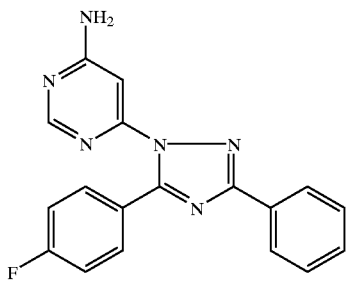

a) (4-Chloropyrimidin-6-yl)hydrazine hydrochloride

Hydrazine hydrate (0.89 ml, 0.92 g, 1.8 mmol) was added to 4,6-dichloropyrimidine (2.5 g, 1.7 mmol) in ethanol (25 ml) at 0° C. After stirring the reaction mixture at this temperature for 0.5 h, the precipitate which formed was collected and washed with ethanol to afford the title compound as a white solid; yield 1.5 g.

b) 1-(4-Chloropyrimidin-6-yl)-3-phenyl-5-(4-fluorophenyl)-1,2,4-triazole

Following the procedure of Example 1b except substituting (4-chloropyrimidin-6-yl)hydrazine hydrochloride for (4-pyridyl)hydrazine afforded the title compound as a white solid in 34% yield: $^1$H NMR ($CDCl_3$) δ8.69 (s, 1H), 8.26 (dd, 2H), 8.07 (s, 1H), 7.71 (dd, 2H), 7.52 (m, 3H), 7.18 (t, 2H).

c) 1-(6-Aminopyrimidin-4-yl)-3-phenyl-5-(4-fluorophenyl)-1,2,4-triazole

A mixture of 1-(4-chloropyrimidin-6-yl)-3-phenyl-5-(4-fluorophenyl)-1,2,4-triazine (0.080 g, 0.23 mmol) and concentrated $NH_4OH$ was heated to 120° C. for 18 h in a sealed reaction vessel. After cooling the reaction to ambient temperature, the precipitate which had formed was collected and washed with water, air-dried and dried in vacuo at 40° C. to afford the title compound as a white solid; yield 0.030 g (39%): ES MS m/z=333 (MH$^+$).

Example 3

1-[4-(6,7-Dimethoxyquinazoline)]-3-phenyl-5-(4-fluorophenyl)-1,2,4-triazole

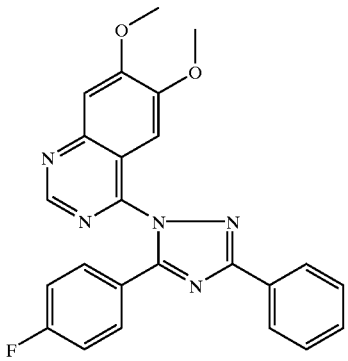

a) 6,7-Dimethoxyquinazoline-1-hydrazine hydrochloride

Chloro-6,7-dimethoxyquinazoline (6 g, 26.79 mmol) and hydrazine monohydrate (2.7 g, 54.79 mmol) in ethanol were stirred together at 75° C. for 3 h. Most of ethanol was evaporated in high vacuo. The resulting solid was washed with hexane (3×). Recrystallization from EtOAc/hexane (1:2) afforded the title compound (5.1 g). ES MS m/z 237 (MH$^+$).

b) 1-[4-(6,7-Dimethoxyquinazoline)]-3-phenyl-5-(4-fluorophenyl)-1,2,4-triazole

The title compound was prepared as described in Example 1b except substituting 6,7-dimethoxyquinazoline-1-hydrazine hydrochloride for (4-pyridyl)hydrazine. m.p. 228–230° C.

All publications, including but not limited to patents and patent applications, cited in this specification are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration, it is believed that one skilled in the are can, using the preceding description, utilize the present invention to its fullest extent. Therefore, the Examples herein are to be construed as merely illustrative and not a limitation of the scope of the present invention in any way. The embodiments of the invention in which an exclusive property or privilege is claimed are defined as follows.

What is claimed is:

1. A compound of the formula:

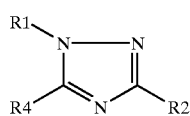

(I)

wherein $R_1$ is a pyrid-4-yl, or a pyrimidin-4-yl ring, which ring is substituted one or more times with Y, and optionally substituted one or more times with $C_{1-4}$ alkyl, halogen, hydroxyl, $C_{1-4}$ alkoxy, $C_{1-4}$ alkylthio, $C_{1-4}$ alkylsulfinyl, $CH_2OR_{12}$, amino, mono and di-$C_{1-6}$ alkyl substituted amino, $N(R_{10})C(O)R_b$ or an N-heterocyclyl ring which ring has from 5 to 7 members and optionally contains an additional heteroatom selected from oxygen, sulfur or $NR_{15}$;

Y is $X_1$-$R_a$;

$X_1$ is sulfur, oxygen, or NH;

$R_a$ is aryl, aryl$C_{1-6}$alkyl, heterocyclic, heterocyclyl$C_{1-6}$ alkyl, heteroaryl, or heteroaryl$C_{1-6}$alkyl, wherein each of these moieties may be optionally substituted;

$R_4$ is phenyl, naphth-1-yl or naphth-2-yl, or a heteroaryl, which is optionally substituted by one or two substituents, each of which is independently selected, and which, for a 4-phenyl, 4-naphth-1-yl, 5-naphth-2-yl or 6-naphth-2-yl substituent, is halogen, cyano, nitro, $C(Z)NR_7R_{17}$, $C(Z)OR_{16}$, $(CR_{10}R_{20})_vCOR_{12}$, $SR_5$, $SOR_5$, $OR_{12}$, halo-substituted-$C_{1-4}$ alkyl, $C_{1-4}$ alkyl, $ZC(Z)R_{12}$, $NR_{10}C(Z)R_{16}$, or $(CR_{10}R_{20})_vNR_{10}R_{20}$ and which, for other positions of substitution, is halogen, cyano, $C(Z)NR_{13}R_{14}$, $C(Z)OR_3$, $(CR_{10}R_{20})_{m''}COR_3$, $S(O)_mR_3$, $OR_3$, halo-substituted-$C_{1-4}$ alkyl, $C_{1-4}$ alkyl, $(CR_{10}R_{20})_{m''}NR_{10}C(Z)R_3$, $NR_{10}S(O)_{m'}R_8$, $NR_{10}S(O)_mNR_7R_{17}$, $ZC(Z)R_3$ or $(CR_{10}R_{20})_{m''}NR_{13}R_{14}$;

Z is oxygen or sulfur;

n is 0, or an integer having a value of 1 to 10;

m is 0, or the integer 1 or 2;

m' is an integer having a value of 1 or 2, m'' is 0, or an integer having a value of 1 to 5;

v is 0, or an integer having a value of 1 or 2;

$R_2$ is hydrogen, $C(H)(A)(R_{22})$, $(CR_{10}R_{23})_nOR_9$, $(CR_{10}R_{23})_nOR_{11}$, $C_{1-10}$alkyl, halo-substituted $C_{1-10}$ alkyl, $C_{2-10}$ alkenyl, $C_{2-10}$ alkynyl, $C_{3-7}$ cycloalkyl, $C_{3-7}$cycloalkyl$C_{1-10}$alkyl, $C_{5-7}$ cycloalkenyl, $C_{5-7}$ cycloalkenyl $C_{1-10}$alkyl, aryl, aryl$C_{1-10}$ alkyl, heteroaryl, heteroaryl$C_{1-10}$ alkyl, heterocyclyl, heterocyclyl$C_{1-10}$ alkyl, $(CR_{10}R_{23})_nS(O)_mR_{18}$, $(CR_{10}R_{23})_nNHS(O)_2R_{18}$, $(CR_{10}R_{23})_nNR_{13}R_{14}$, $(CR_{10}R_{23})_nNO_2$, $(CR_{10}R_{23})_nCN$, $(CR_{10}R_{23})_nS(O)_mNR_{13}R_{14}$, $(CR_{10}R_{230})_nC(Z)R_{11}$, $(CR_{10}R_{23})_nOC(Z)R_{11}$, $(CR_{10}R_{23})_nC(Z)OR_{11}$, $(CR_{10}R_{23})_nC(Z)NR_{13}R_{14}$, $(CR_{10}R_{23})_nC(Z)NR_{11}OR_9$, $(CR_{10}R_{23})_nNR_{10}C(Z)R_{11}$, $(CR_{10}R_{23})_nNR_{10}C(Z)NR_{13}R_{14}$, $(CR_{10}R_{23})_nN(OR_6)C(Z)NR_{13}R_{14}$, $(CR_{10}R_{23})_nN(OR_6)C(Z)R_{11}$, $(CR_{10}R_{23})_nC(=NOR_6)R_{11}$, $(CR_{10}R_{23})_nNR_{10}C(=NR_{19})NR_{13}R_{14}$, $(CR_{10}OR_{23})_nOC(Z)NR_{13}R_{14}$, $(CR_{10}R_{23})_nNR_{10}C(Z)NR_{13}R_{14}$, $(CR_{10}R_{23})_nNR_{10}C(Z)OR_{10}$, 5-($R_{18}$)-1,2,4-oxadizaol-3-yl or 4-($R_{12}$)-5-($R_{18}R_{19}$)-4,5-dihydro-1,2,4-oxadiazol-3-yl; wherein the cycloalkyl, cycloalkylalkyl, aryl, arylalkyl, heteroaryl, heteroaryl alkyl, heterocyclic and heterocyclic alkyl groups may be optionally substituted;

A is an optionally substituted aryl, heterocyclyl, or heteroaryl ring, or A is a substituted $C_{1-10}$ alkyl;

$R_{22}$ is an optionally substituted $C_{1-10}$ alkyl;

$R_b$ is hydrogen, $C_{1-6}$ alkyl, $C_{3-7}$ cycloalkyl, aryl, aryl$C_{1-4}$ alkyl, heteroaryl, heteroaryl$C_{1-4}$alkyl, heterocyclyl, or heterocyclyl$C_{1-4}$ alkyl; and wherein each of these moieties may be optionally substituted;

$R_3$ is heterocyclyl, heterocyclyl$C_{1-10}$ alkyl or $R_8$;

$R_5$ is hydrogen, $C_{1-4}$ alkyl, $C_{2-4}$ alkenyl, $C_{2-4}$ alkynyl or $NR_7R_{17}$, excluding the moieties $SR_5$ being $SNR_7R_{17}$ and $SOR_5$ being SOH;

$R_6$ is hydrogen, a pharmaceutically acceptable cation, $C_{1-10}$ alkyl, $C_{3-7}$ cycloalkyl, aryl, aryl$C_{1-4}$ alkyl, heteroaryl, heteroaryl$C_{1-4}$ alkyl, heterocyclic, aroyl, or $C_{1-10}$ alkanoyl;

$R_7$ and $R_{17}$ is each independently selected from hydrogen or $C_{1-4}$ alkyl or $R_7$ and $R_{17}$ together with the nitrogen to which they are attached form a heterocyclic ring of 5 to 7 members which ring optionally contains an additional heteroatom selected from oxygen, sulfur or $NR_{15}$;

$R_8$ is $C_{1-10}$ alkyl, halo-substituted $C_{1-10}$ alkyl, $C_{2-10}$ alkenyl, $C_{2-10}$ alkynyl, $C_{3-7}$ cycloalkyl, $C_{5-7}$ cycloalkenyl, aryl, aryl$C_{1-10}$ alkyl, heteroaryl, heteroaryl$C_{1-10}$ alkyl, $(CR_{10}R_{20})_nOR_{11}$, $(CR_{10}R_{20})_nS(O)_mR_{18}$, $(CR_{10}R_{20})_nNHS(O)_2R_{18}$, $(CR_{10}R_{20})_nNR_{13}R_{14}$; and wherein the aryl, arylalkyl, heteroaryl, or heteroaryl alkyl moieties may be optionally substituted;

$R_9$ is hydrogen, $C(Z)R_{11}$ or optionally substituted $C_{1-10}$ alkyl, $S(O)_2R_{18}$, optionally substituted aryl or optionally substituted aryl-$C_{1-4}$ alkyl;

$R_{10}$ and $R_{20}$ are each independently selected from hydrogen or $C_{1-4}$ alkyl;

$R_{11}$ is hydrogen, $C_{1-10}$ alkyl, $C_{3-7}$ cycloalkyl, heterocyclyl, heterocyclyl $C_{1-10}$alkyl, aryl, aryl$C_{1-10}$ alkyl, heteroaryl or heteroaryl$C_{1-10}$ alkyl, wherein all of these moieties may be optionally substituted;

$R_{12}$ is hydrogen or $R_{16}$;

$R_{13}$ and $R_{14}$ is each independently selected from hydrogen or optionally substituted $C_{1-4}$ alkyl, optionally substituted aryl or optionally substituted aryl-$C_{1-4}$ alkyl, or together with the nitrogen which they are attached form a heterocyclic ring of 5 to 7 members which ring optionally contains an additional heteroatom selected from oxygen, sulfur or $NR_9$;

$R_{15}$ is $R_{10}$ or $C(Z)$-$C_{1-4}$ alkyl;

$R_{16}$ is $C_{1-4}$ alkyl, halo-substituted-$C_{1-4}$ alkyl, or $C_{3-7}$ cycloalkyl;

$R_{18}$ is $C_{1-10}$ alkyl, $C_{3-7}$ cycloalkyl, heterocyclyl, aryl, aryl$_{1-10}$alkyl, heterocyclyl, heterocyclyl-$C_{1-10}$alkyl, heteroaryl or heteroaryl$_{1-10}$alkyl;

$R_{19}$ is hydrogen, cyano, $C_{1-4}$ alkyl, $C_{3-7}$ cycloalkyl or aryl;

$R_{23}$ is $C_{1-6}$ alkyl, $C_{3-7}$ cycloalkyl, aryl, aryl$C_{1-4}$ alkyl, heteroaryl, heteroaryl$C_{1-4}$alkyl, heterocyclyl, or a heterocyclyl$C_{1-4}$ alkyl moiety, wherein all of these moieties may be optionally substituted;

or a pharmaceutically acceptable salt thereof.

2. The compound according to claim 1 wherein $R_1$ is an optionally substituted pyrid-4-yl.

3. The compound according to claim 1 wherein $R_1$ is an optionally substituted pyrimidin-4-yl.

4. The compound according to claim 1 wherein the $X_1$ is nitrogen or oxygen.

5. The compound according to claim 4 wherein the $R_a$ moiety is aryl, or arylalkyl.

6. The compound according to claim 1 wherein $R_4$ is an optionally substituted phenyl.

7. The compound according to claim 6 wherein the phenyl is substituted one or more times independently by halogen, $SR_5$, $S(O)R_5$, $OR_{12}$, halo-substituted-$C_{1-4}$ alkyl, or $C_{1-4}$ alkyl.

8. The compound according to claim 1 wherein $R_2$ is hydrogen, $C(H)(A)(R_{22})$, aryl, arylalkyl, heterocyclic, heterocyclicalkyl, heteroaryl and heterocyclic alkyl; and wherein the aryl, heteroaryl or heterocyclic containing moieties may be optionally substituted.

9. The compound according to claim 8 wherein $R_2$ is an optionally substituted aryl.

10. A pharmaceutical composition comprising an effective amount of a compound according to any of claims 1 to 9 and a pharmaceutically acceptable carrier or diluent.

11. A method of treating a CSBPJRK/p38 kinase mediated disease in a mammal in need thereof, which method comprises administering to said mammal an effective amount of a compound of Formula (I) according to claim 1.

12. The method according to claim 11 wherein the CSBP/RK/p38 kinase mediated disease is psoriatic arthritis, Reiter's syndrome, rheumatoid arthritis, gout, traumatic arthritis, rubella arthritis and acute synovitis, rheumatoid spondylitis, osteoarthritis, gouty arthritis and other arthritic condition, sepsis, septic shock, endotoxic shock, gram negative sepsis, toxic shock syndrome, Alzheimer's disease, stroke, neurotrauma, asthma, adult respiratory distress syndrome, cerebral malaria, chronic pulmonary inflammatory disease, silicosis, pulmonary sarcososis, bone resorption disease, osteoporosis, restenosis, CNS injury, cardiac and renal reperfusion injury, chronic renal failure, congestive heart failure, angiogenic diseases, thrombosis, glomerularnephritis, diabetes, graft vs. host reaction, allograft rejection, inflammatory bowel disease, Crohn's disease, ulcerative colitis, multiple sclerosis, muscle degeneration, eczema, contact dermitits, psoriasis, sunburn, conjunctivitis, or rhinovirus infection.

13. A compound of the formula:

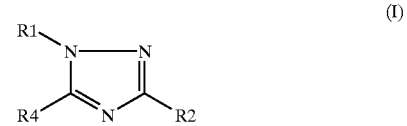

(I)

wherein $R_1$ is a pyrid-4-yl, or a pyrimidin-4-yl ring, which ring is optionally substituted one or more times with Y, $C_{1-4}$ alkyl, halogen, hydroxyl, $C_{1-4}$ alkoxy, $C_{1-4}$ alkylthio, $C_{1-4}$ alkylsulfinyl, $CH_2OR_{12}$, amino, mono and di-$C_{1-6}$ alkyl substituted amino, $N(R_{10})C(O)R_b$ or an N-heterocyclyl ring which ring has from 5 to 7 members and optionally contains an additional heteroatom selected from oxygen, sulfur or $NR_{15}$;

Y is $X_1$-$R_a$;

$X_1$ is sulfur, oxygen, or NH;

$R_a$ is $C_{1-6}$ alkyl, aryl, aryl$C_{1-6}$alkyl, heterocyclic, heterocyclyl$C_{1-6}$alkyl, heteroaryl, or heteroaryl$C_{1-6}$alkyl, wherein each of these moieties may be optionally substituted;

$R_4$ is phenyl, naphth-1-yl or naphth-2-yl, or a heteroaryl, which is optionally substituted by one or two substituents, each of which is independently selected, and which, for a 4-phenyl, 4-naphth-1-yl, 5-naphth-2-yl or 6-naphth-2-yl substituent, is halogen, cyano, nitro, $C(Z)NR_7R_{17}$, $C(Z)OR_{16}$, $(CR_{10}R_{20})_vCOR_{12}$, $SR_5$, $SOR_5$, $OR_{12}$, halo-substituted-$C_{1-4}$ alkyl, $C_{1-4}$ alkyl, $ZC(Z)R_{12}$, $NR_{10}C(Z)R_{16}$, or $(CR_{10}R_{20})_vNR_{10}R_{20}$ and which, for other positions of substitution, is halogen, cyano, $C(Z)NR_{13}R_{14}$, $C(Z)OR_3$, $(CR_{10}R_{20})_{m''}COR_3$, $S(O)_mR_3$, $OR_3$, halo-substituted-$C_{1-4}$ alkyl, $C_{1-4}$ alkyl, $(CR_{10}R_{20})_{m''}NR_{10}C(Z)R_3$, $NR_{10}S(O)_{m'}R_8$, $NR_{10}S(O)_{m'}NR_7R_{17}$, $ZC(Z)R_3$ or $(CR_{10}R_{20})_{m''}NR_{13}R_{14}$;

Z is oxygen or sulfur;

n is 0, or an integer having a value of 1 to 10;

m is 0, or the integer 1 or 2;

m' is an integer having a value of 1 or 2, m" is 0, or an integer having a value of 1 to 5;

v is 0, or an integer having a value of 1 or 2;

$R_2$ is hydrogen, or $C(H)(A)(R_{22})$;

A is an optionally substituted aryl, heterocyclyl, or heteroaryl ring, or A is a substituted $C_{1-10}$ alkyl;

$R_{22}$ is an optionally substituted $C_{1-10}$ alkyl;

$R_b$ is hydrogen, $C_{1-6}$ alkyl, $C_{3-7}$ cycloalkyl, aryl, arylC$_{1-4}$ alkyl, heteroaryl, heteroarylC$_{1-4}$alkyl, heterocyclyl, or heterocyclyC$_{1-4}$ alkyl; and wherein each of these moieties may be optionally substituted;

$R_3$ is heterocyclyl, heterocyclylC$_{1-10}$ alkyl or $R_8$;

$R_5$ is hydrogen, $C_{1-4}$ alkyl, $C_{2-4}$ alkenyl, $C_{2-4}$ alkynyl or $NR_7R_{17}$, excluding the moieties $SR_5$ being $SNR_7R_{17}$ and $SOR_5$ being SOH;

$R_6$ is hydrogen, a pharmaceutically acceptable cation, $C_{1-10}$ alkyl, $C_{3-7}$ cycloalkyl, aryl, arylC$_{1-4}$ alkyl, heteroaryl, heteroarylC$_{1-4}$ alkyl, heterocyclic, aroyl, or $C_{1-10}$ alkanoyl;

$R_7$ and $R_{17}$ is each independently selected from hydrogen or $C_{1-4}$ alkyl or $R_7$ and $R_{17}$ together with the nitrogen to which they are attached form a heterocyclic ring of 5 to 7 members which ring optionally contains an additional heteroatom selected from oxygen, sulfur or $NR_{15}$;

$R_8$ is $C_{1-10}$ alkyl, halo-substituted $C_{1-10}$ alkyl, $C_{2-10}$ alkenyl, $C_{2-10}$ alkynyl, $C_{3-7}$ cycloalkyl, $C_{5-7}$ cycloalkenyl, aryl, arylC$_{1-10}$ alkyl, heteroaryl, heteroarylC$_{1-10}$ alkyl, $(CR_{10}R_{20})_nOR_{11}$, $(CR_{10}R_{20})_nS(O)_mR_{18}$, $(CR_{10}R_{20})_nNHS(O)_2R_{18}$, $(CR_{10}R_{20})_nNR_{13}R_{14}$; and wherein the aryl, arylalkyl, heteroaryl, or heteroaryl alkyl moieties may be optionally substituted;

$R_9$ is hydrogen, $C(Z)R_{11}$ or optionally substituted $C_{1-10}$ alkyl, $S(O)_2R_{18}$, optionally substituted aryl or optionally substituted aryl-$C_{1-4}$ alkyl;

$R_{10}$ and $R_{20}$ are each independently selected from hydrogen or $C_{1-4}$ alkyl;

$R_{11}$ is hydrogen, $C_{1-10}$ alkyl, $C_{3-7}$ cycloalkyl, heterocyclyl, heterocyclyl $C_{1-10}$alkyl, aryl, arylC$_{1-10}$ alkyl, heteroaryl or heteroarylC$_{1-10}$ alkyl, wherein all of these moieties may be optionally substituted;

$R_{12}$ is hydrogen or $R_{16}$;

$R_{13}$ and $R_{14}$ is each independently selected from hydrogen or optionally substituted $C_{1-4}$ alkyl, optionally substituted aryl or optionally substituted aryl-$C_{1-4}$ alkyl, or together with the nitrogen which they are attached form a heterocyclic ring of 5 to 7 members which ring optionally contains an additional heteroatom selected from oxygen, sulfur or $NR_9$;

$R_{15}$ is $R_{10}$ or $C(Z)$-$C_{1-4}$ alkyl;

$R_{16}$ is $C_{1-4}$ alkyl, halo-substituted-$C_{1-4}$ alkyl, or $C_{3-7}$ cycloalkyl;

$R_{18}$ is $C_{1-10}$ alkyl, $C_{3-7}$ cycloalkyl, heterocyclyl, aryl, aryl$_{1-10}$ alkyl, heterocyclyl, heterocyclyl-$C_{1-10}$ alkyl, heteroaryl or heteroaryl$_{1-10}$alkyl;

$R_{19}$ is hydrogen, cyano, $C_{1-4}$ alkyl, $C_{3-7}$ cycloalkyl or aryl;

$R_{23}$ is hydrogen, $C_{1-6}$ alkyl, $C_{3-7}$ cycloalkyl, aryl, arylC$_{1-4}$ alkyl, heteroaryl, heteroarylC$_{1-4}$alkyl, heterocyclyl, or a heterocyclylC$_{1-4}$ alkyl moiety, wherein all of these moieties may be optionally substituted;

or a pharmaceutically acceptable salt thereof.

14. The compound according to claim 13 wherein $R_1$ is an optionally substituted pyrid-4-yl.

15. The compound according to claim 13 wherein $R_1$ is an optionally substituted pyrimidin-4-yl.

16. The compound according to any one of claims 13 to 15 wherein the $R_1$ substituent is Y.

17. The compound according to claim 16 wherein the Ra moiety is alkyl, aryl, or arylalkyl.

18. The compound according to claim 13 wherein $R_4$ is an optionally substituted phenyl.

19. The compound according to claim 18 wherein the phenyl is substituted one or more times independently by halogen, $SR_5$, $S(O)R_5$, $OR_{12}$, halo-substituted-$C_{1-4}$ alkyl, or $C_{1-4}$ alkyl.

20. The compound according to claim 13 wherein $R_2$ is $C(AA1)(A)$, and AA1 is $R_{22}$, and is the side chain residue of an amino acid.

21. The compound according to claim 20 wherein both A and $R_{22}$ are $C_{1-6}$ alkyl OR11.

22. The compound according to claim 13 which is:
1-(Pyrid-4-yl)-3-phenyl-5-(4-fluorophenyl)-1,2,4-triazole;
1-(6-Aminopyrimidin-4-yl)-3-phenyl-5-(4-fluorophenyl)-1,2,4-triazole;
or a pharmaceutically acceptable salt thereof.

23. The method according to claim 25 wherein the compound of Formula (I) is
1-(Pyrid-4-yl)-3-phenyl-5-(4-fluorophenyl)-1,2,4-triazole;
1-(6-Aminopyrimidin-4-yl)-3-phenyl-5-(4-fluorophenyl)-1,2,4-triazole;
or a pharmaceutically acceptable salt thereof.

24. A pharmaceutical composition comprising an effective amount of a compound according to any one of claims 13 to 21 and a pharmaceutically acceptable carrier or diluent.

25. A method of treating a CSBP/RK/p38 kinase mediated disease in a mammal in need thereof, which method comprises administering to said mammal an effective amount of a compound of Formula (I) according to any one of claims 13 to 24.

26. The method according to claim 25 wherein the CSBP/RK/p38 kinase mediated disease is psoriatic arthritis, Reiter's syndrome, rheumatoid arthritis, gout, traumatic arthritis, rubella arthritis and acute synovitis, rheumatoid spondylitis, osteoarthritis, gouty arthritis and other arthritic condition, sepsis, septic shock, endotoxic shock, gram negative sepsis, toxic shock syndrome, Alzheimer's disease, stroke, neurotrauma, asthma, adult respiratory distress, syndrome, cerebral malaria, chronic pulmonary inflammatory disease, silicosis, pulmonary sarcososis, bone resorption disease, osteoporosis, restenosis, CNS injury, cardiac and renal reperfusion injury, chronic renal failure, congestive heart failure, angiogenic diseases, thrombosis, glomerularnephritis, diabetes, graft vs. host reaction, allograft rejection, inflammatory bowel disease, Crohn's disease, ulcerative colitis, multiple sclerosis, muscle degeneration, eczema, contact dermititis, psoriasis, sunburn, conjunctivitis, or rhinovirus infection.

* * * * *